US011471267B2

(12) United States Patent
Gordon

(10) Patent No.: US 11,471,267 B2
(45) Date of Patent: Oct. 18, 2022

(54) HIGH-PROFILE, ANATOMY-SPECIFIC CRANIOFACIAL IMPLANTS FOR COMBINED HARD AND SOFT TISSUE RECONSTRUCTION WITH EMBEDDED TECHNOLOGY FOR MEDICINE DELIVERY

(71) Applicant: CraniUS LLC, Baltimore, MD (US)

(72) Inventor: Chad Gordon, Cockeysville, MD (US)

(73) Assignee: CraniUS LLC, Baltimore, MD (US)

( * ) Notice: Subject to any disclaimer, the term of this patent is extended or adjusted under 35 U.S.C. 154(b) by 0 days.

(21) Appl. No.: 17/400,239

(22) Filed: Aug. 12, 2021

(65) Prior Publication Data

US 2022/0047378 A1 Feb. 17, 2022

Related U.S. Application Data

(60) Provisional application No. 63/065,045, filed on Aug. 13, 2020.

(51) Int. Cl.
*A61F 2/28* (2006.01)
*A61F 2/08* (2006.01)
*A61F 2/30* (2006.01)

(52) U.S. Cl.
CPC .......... *A61F 2/0811* (2013.01); *A61F 2/2875* (2013.01); *A61F 2002/0817* (2013.01);
(Continued)

(58) Field of Classification Search
CPC .................. A61F 2/0811; A61F 2/2875; A61F 2002/0817; A61F 2002/0894; A61F 2002/3068
See application file for complete search history.

(56) References Cited

U.S. PATENT DOCUMENTS 5,727,567 A * 3/1998 Carnaby ................. A61F 2/105
602/17
7,004,948 B1 * 2/2006 Pianca ............... A61B 17/3462
607/116
(Continued)

FOREIGN PATENT DOCUMENTS

WO 2020223126 A1 11/2020

OTHER PUBLICATIONS

Notification of Transmittal of the International Search Report and the Written Opinion of the International Searching Authority dated Nov. 24, 2021, in connection with corresponding international Application No. PCT/US2021/045672 (14 pp.).

*Primary Examiner* — Yashita Sharma
*Assistant Examiner* — Melissa A Hoban
(74) *Attorney, Agent, or Firm* — Maier & Maier, PLLC

(57) ABSTRACT

An anatomy-specific implant for neuroplastic surgery. The implant includes a soft tissue implant component designed within and adapted to replace or restore missing soft tissue in a skull, joint or spine of the patient, wherein the soft tissue implant component is adapted to be coupled by an interdigitated connection to a rigid component. The rigid component can be a skull implant adapted to replace missing cranial or vertebral bone, or healthy cranial or vertebral bone, either of which can have downward extending catheters for medicinal brain or spinal cord infusion to help bypass the blood-brain barrier via multiphase flow. The soft tissue implant may include a functional component having neurotechnologies such as MRI-lucent pumps, Bluetooth connection systems, refillable diaphragms, remote imaging devices, wireless charging capabilities, and/or informative biosensors. The soft tissue implant component may be interchangeable with another soft tissue implant component in plug-and-play fashion.

15 Claims, 8 Drawing Sheets

(52) U.S. Cl.
    CPC ............... *A61F 2002/0894* (2013.01); *A61F 2002/3068* (2013.01)

(56) References Cited

U.S. PATENT DOCUMENTS

| | | | | |
|---|---|---|---|---|
| 7,346,391 | B1* | 3/2008 | Osorio | A61B 5/6864 607/139 |
| 8,454,701 | B2* | 6/2013 | Devauchelle | A61N 1/0529 623/17.19 |
| 2003/0039676 | A1* | 2/2003 | Boyce | A61F 2/32 623/16.11 |
| 2006/0224242 | A1* | 10/2006 | Swords | A61L 27/446 606/915 |
| 2007/0213783 | A1* | 9/2007 | Pless | A61N 5/0622 607/42 |
| 2008/0140149 | A1* | 6/2008 | John | A61B 8/0808 607/45 |
| 2010/0023130 | A1 | 1/2010 | Henry et al. | |
| 2012/0259428 | A1 | 10/2012 | Brogan et al. | |
| 2014/0194720 | A1* | 7/2014 | Hua | A61B 5/6882 607/45 |
| 2014/0309744 | A1* | 10/2014 | Batty | A61F 2/2875 623/17.19 |
| 2015/0045897 | A1* | 2/2015 | Gordon | A61F 2/2875 700/98 |
| 2016/0361523 | A1* | 12/2016 | Haughton | A61M 27/006 |
| 2018/0055640 | A1 | 3/2018 | Gordon et al. | |
| 2018/0325672 | A1* | 11/2018 | Gordon | A61F 2/2875 |
| 2018/0338835 | A1 | 11/2018 | Gordon | |
| 2019/0209328 | A1 | 7/2019 | Christopher et al. | |
| 2020/0054454 | A1* | 2/2020 | D'Urso | A61B 5/291 |
| 2021/0260280 | A1* | 8/2021 | Gordon | A61M 39/0247 |

* cited by examiner

HIGH-PROFILE, ANATOMY-SPECIFIC CRANIOFACIAL IMPLANTS FOR COMBINED HARD AND SOFT TISSUE RECONSTRUCTION WITH EMBEDDED TECHNOLOGY FOR MEDICINE DELIVERY

CROSS-REFERENCE TO RELATED APPLICATIONS

This application claims priority to U.S. Provisional Application No. 63/065,045, filed Aug. 13, 2020, and entitled "Multi-Purpose, Anatomic-Specific Implants for Combined Hard and Soft Tissue Reconstruction with Embedded Technologies for Improving Form and Function", the entire contents of which are hereby incorporated by reference.

FIELD

The embodiments generally relate to the field of chronic medicine delivery, refillable needle reservoirs, wearable technology, Bluetooth-enabled devices, wireless charging power platforms, state-of-the-art biotechnology, craniofacial implants, neurosurgery, neuroplastic surgery, implantable neurotechnology, plastic surgery, craniomaxillofacial surgery, orthopedic surgery and neuro-oncology, and specifically to the field of improving form and function of permanent implants for anatomical replacement of both hard and soft tissue components.

BACKGROUND

Modern day man-made implants have been designed for anatomical replacement with respect to the bone (i.e., hard tissue) defects which they replace. For example, the present inventor has invented the low-profile intercranial device, described in U.S. Pat. No. 11,058,541, issued on Jul. 13, 2021, which discloses placing implantable technologies within the hard tissue (cranial bone space) and is described specifically as "an implant for which substantially conforms with a resected portion of a skull of a patient". However, as the technology has moved forward with respect to miniaturization, a less invasive option would be to use a combined soft and hard tissue anatomical component within the temporal fossa as an improved strategy to prevent the surgeon from having to remove large segments of bone to make room for the low-profile intercranial device. For example, the present invention may utilize combined soft tissue replacement thereby allowing for a small amount of bone space utilization, versus the more invasive option, which is using a large segment of cranial bone resection to make room for embedded neurotechnology; furthermore, soft tissue space utilization may be much safer for the patient.

The present invention is pre-designed using anatomical compartment sizes matching the typical adult male and female, as opposed to the present inventor's prior invention, "Patient-specific Craniofacial Implants", described in U.S. Pat. No. 10,918,485, issued on Feb. 16, 2021. The prior invention discloses using the temporal soft tissue space in combination with the hard tissue (bone) space, but is only limited to a "patient-specific" (i.e., custom) design. In contrast, the present invention can use an identical temporal augmentation volume and implant design; however, it may be offered both in both "anatomy-specific" (i.e., non-customized) and "patient-specific" (i.e., customized) embodiments. The implants according to the present invention may either be pre-designed using computer-assisted design/manufacturing (CAD/CAM) as customized, patient-specific implants, or can be pre-designed as anatomy-specific implants using anatomical averaging. The present invention may employ anatomical averaging to accomplish an "off-the-shelf", one-size-fits-all implant. Embodiments of the present invention may partially fill some missing bone, but will also fill partially some missing soft tissue, e.g., temporalis muscle and/or temporal fat pad. This type of implant manufacturing process may equate to a pre-fabricated device and/or implant manufactured from a safe, biocompatible, alloplastic material which may hold a permanent shape and form with respect to time, regardless of bio-engineered internal movements (i.e., chronic, direct, pump-assisted, medicine delivery via several connected catheters extending deep to within the neighboring brain's white matter as a way to bypass the blood-brain barrier), and/or subsequent mechanical trauma (i.e., the outer casing shell surrounding the medicine delivery components are designed to fit snugly within and have internal buttressing within the hollow space for which remains stable in the setting of inadvertent head trauma). Notably, utilization of the soft tissue space, in addition to the cranial bone space, provides the ideal, non-obvious solution for placement at the smallest distance away from the brain (i.e., there is no closer space to the temporal lobe of the brain than the temporal cranial bone and temporal soft tissue). Hence, from an engineering perspective, the design and safety of the present invention is greatly increased given that the conduit (i.e., catheters) for medicine delivery can be made much shorter and thus the flow is much more predictable.

However, up until recently, there have been no "anatomy-specific craniofacial implants" or devices that were pre-designed for the temporal region with medicine pumps for convection-enhanced delivery to the brain and/or internal biosensors for improving both form and function of one's head in the setting of intracranial pressure changes (i.e., hydrocephalus, bleeding, tumor growth, change in altitude, seizures, etc.), and, at the same time, strategically designed to replace both the temporal hard (i.e., bone) and soft tissue (i.e., temporalis muscle, temporal fat pad, and subcutaneous tissue) defects simultaneously in a way that camouflages the device itself completely from the naked eye with absent deformity. In fact, the first-ever case scenario using a bone replacement implant, with embedded biosensor design, was surgically performed by the present inventor (Gordon C R, et al. "First in-human experience with integration of wireless intracranial pressure monitoring device within a customized cranial implant." *Operative Neurosurgery* 2020 Jan. 28). In addition, the present inventor was also the first to describe "Patient-specific Craniofacial Implants" (U.S. Pat. No. 10,639,158) for replacing both missing temporal bone and soft tissue in the craniofacial region. However, this prior invention was strictly limited to a customized solution addressing a problem for a hard and soft tissue scenario, as opposed to the present invention, which is non-customized, but is rather designed based on normative volumes applied to temporal hard (bone) and soft (muscle/fat) tissue. While a patient-specific implant is customized by a pre-operative CT scan and CAD/CAM modeling based on individualized findings, the anatomy-specific implant of present invention may be pre-fabricated using normative values and human atlas data to accomplish a similar result with similar efficacy and similar effect, but with less labor or lead time needed for implant availability. Notably, the "patient-specific craniofacial implant" patented invention takes on average 3 days to 3 weeks to design, fabricate and deliver, where as the "anatomy-specific" design in this instance described here can be pre-fabricated well in advance and is therefore a much simpler "right sided" or left sided" temporal implant with immediate availability, and can be with or without the use of embedded technologies within for medicine delivery.

Bony anatomies constructing certain aspects of the human head maintain a constant form, and thus lend themselves well to the field of implantable implants and devices in that their shape and form stay ever-constant. For example, an embodiment of the present invention describes a device with a hard-shell, curved case that is internally hollowed strategically to support internal workings consistent with pump-assisted technology for brain medicine delivery. Conversely, soft tissue areas found over the craniofacial bone, such as with the temporalis muscle, temporal fat pad, and temporal subcutaneous tissue, are constantly changing in shape depending on one's age and/or bodily movements throughout the day, and therefore have inconsistent boundaries challenging the task of implant design. As such, the use of temporal soft tissue spaces was not described in the present inventor's published patent application entitled "Magnetic resonance imaging compatible, convection-enhanced delivery cranial implant devise and related methods" [WO-20200006240-A1] as it was initially believed that the cranial device could be used to replace one's skull. After further consideration, the present inventor determined that an optimal implant design to achieve direct brain medicine delivery requires the use of the temporal soft tissue space. Thus, the present invention may replace the normal soft tissue within the temporal fossa with hard-plastic devices, but with a shape that camouflages placement and may remove signs of visible deformity (i.e., neuroplastic surgery practice and principles). According to the disclosure herein, a pre-fabricated multipurpose device may be designed—in non-customized fashion, thereby allowing "off-the-shelf", easy availability—via a novel design algorithm related to human normative data (i.e., anatomical averaging) including several imaging modalities such as computed topography (CT) scanning or magnetic-resonance imaging (MRI). Specifically, bony landmarks and anatomical confines of the craniofacial skeleton are best understood using CT, and soft tissue landmarks and anatomical confines are best understood using MRI. Thus, an embodiment of the temporal device disclosed herein may be made to simultaneously 1) replace hard and soft tissue (in both pre-existing and non-existing scenarios) using the aforementioned advances by the present inventor; 2) contain embedded technologies like internal electro-osmotic pumps with non-ferrous components, biosensors for important wireless data collection like internal flow rate, systems capable of pump-assisted, multiphase flow, convection-enhanced medicine delivery, and/or embedded ultrasound arrays for remote brain imaging using the aforementioned advances by the present inventor to help determine if and when recurrent brain tumors are regrowing unaffected by the local chemotherapy delivery; and 3) using the embedded technological elements for medicine delivery to improve form and function simultaneously so that it is not visible to an outside party that the patient is receiving direct brain medicine delivery and that there is a refillable diaphragm for needle puncture just a few millimeters below the skin of the patient's scalp. Notably, in the present inventor's previous application, "Magnetic resonance imaging compatible, convection-enhanced delivery cranial implant devise and related methods" [WO-20200006240-A1], the cranial device was envisioned to be placed within the skull underneath the hair-bearing scalp. However, the present inventor has realized that the such is a suboptimal design and one that would severely challenge the healthcare provider when and/if trying to palpate and inject medicine through the scalp. Instead, the present inventor has determined that a high-profile, temporal implant replacing both the hard and soft tissue would position the medicine delivery implant in the temporal region, which is an anatomical area devoid of hair, easier to locate by palpation, and most importantly, the medicine injection process would be less cumbersome and more safe, free of hair and potential bacteria contamination. Furthermore, having a "high-profile" aspect of the implant (i.e., extending through and reconstructing the soft tissue space) allows for the device to extend just underneath the skin, which can be valuable for several reasons such as easier/safer access for percutaneous needle entry for medicine refilling, as well as providing a shorter distance/less tissue interference when it comes to wireless charging and/or Bluetooth wireless communication.

Of note, a craniofacial implant limited to the "intercranial" region, such as the present inventor's prior invention of a low profile intercranial device, fails to provide the correct access point for this type of medicine-delivery invention. For instance, it's the extension of the present implant's boundaries moving outward, upward, and laterally beyond the previously-described skull bone space (i.e., the present implant design now being "extracranial" instead of "intercranial"), and instead now also replacing temporalis muscle, temporal fat, and temporal scalp subcutaneous tissue thereby reaching all the way up to just under the temporal scalp/face skin, which in turn, provides a major difference and benefit by now allowing a short, non-boring needle to puncture the skin safely and quickly enter the refillable valve just a millimeter or two below the skin—in a minimally-invasive way. In contrast, refilling a "low profile intercranial device" would be a much invasive given that the needle would need to transverse the entire scalp tissue all the way down to the level of the bone-containing implant. Furthermore, the entry point along the temporal region—for a "low-profile intercranial device"—would be dangerously obstructed by the temporalis muscle, the temporal fat pad, and the temporal subcutaneous tissue. This would cause the patient pain and bleeding each and every time the needle was used to refill the medicine port. As such, the present inventor posits that to safely achieve medicine delivery to the brain via a simple, quick, refillable reservoir an anatomy-specific temporal implant such as the present invention is needed. Advantages of the present invention include using the temporal fossa location point and this novel temporal implant design as an enhanced strategy for combined hard and soft tissue replacement thereby preventing visible deformity; providing safe access to percutaneous needle sticks given there is only thin temporal skin covering the implant versus a full-thickness, hair-bearing scalp; and 3) provides an exponential increase in internal volume for embedded pump-assisted technology to fit within unlike the use of the "intercranial device" space limited by human skull dimensions.

Systemic delivery of medication to the brain is hindered by the blood-brain barrier's highly selective permeability, which allows the highly-specified passage of only certain materials from capillary blood into the brain's extracellular fluid with just a relative fraction of less than 99%. In fact, recent reports state that over 60% of all pharmaceutical laboratories specific to neurologic medicine development are shutting down on an annual basis due to the complicated, gridlock barriers preventing successful delivery of blood-based medicines into the brain. As such, much work has been focused on engineering medicinal compositions to be small and hydrophobic enough to diffuse through the endothelial cells that make up the complex blood-brain barrier. However, this has been suboptimal since many of the medicinally advantageous compositions are simply too large or hydrophilic and cannot be engineered for such direct delivery to the brain. Thus, in 1994, Dr. Oldfield at the NIH was the world's first scientist to introduce a new method known as "convection-enhanced delivery" as a way to bypass the blood brain barrier and to directly convect (i.e., provide multiphase flow) medicine from a pump through a single catheter directly into the white matter of the brain, so as to skip the blood vessel route altogether (Bobo R H, Laske D W, Akbasak A A, Morrison P F, Dedrick R L, Oldfield E H. "*Convection-enhanced delivery of macromolecules in the brain*". Proc Natl Acad Sci USA. 91(6):2076-80). Oldfield and colleagues reported first-ever success in opening the scalp and removing the skull in several cats and using a single-catheter system with a pump to effectively convect medicine at a rate ranging from 0.5-1.0 microliters/minute, as a way to successful bypass the blood-brain barrier. Although remarkably successful, the cat could only survive for 24 hours given the invasive nature, infectious risks, and extra-anatomical design constraints set for by the pump-assisted technology. Thus, in the neuroscience field for the last three decades, long-term convection-enhanced delivery has remained promising but unachievable in humans, as a proper anatomical positioning and space needed to make room for such device implantation had not been conceived [Bruce et al. Convection enhanced delivery. Neurotherapeutics 2017; 14:358-371]. Prior to the present invention, an anatomic-specific, multi-purpose design to accommodate MRI-lucent pump technology by way of incorporating the temporal bone, temporalis muscle, and the temporal fat pad in its design algorithm has not been envisioned. In other words, one was not able to discover a reliable method and device capable of chronic "convection-enhanced delivery" given the unique size constraints within the human head or skull. For instance, the present inventor's prior invention, the low-profile intercranial device, was limited to a vertical size of about 4-12 millimeters (i.e., thickness) given the constraints of the intercranial bone space. In contrast, the present invention's provision of a device design compatible with combined hard and soft tissue spaces can now instead allow important high-profile device medicine delivery to occur within the brain and body, by providing triple the available volume for internal housing (between about 12-40 millimeters in thickness). The addition of temporal muscle and temporal fat replacement adds a several-fold increase in internal space and thereby drastically improves the odds of safe, pump-assisted, medicine delivery to the brain, as well as provides additional space for synergistic technologies like ultrasound probes (to detect brain tumor recurrence) and biosensors (to detect too much or too little medicine delivery). As such, it requires a high-profile contour that extends way beyond the limits of the cranial bone space and should therefore be termed "extracranial" in design (i.e., as opposed to being limited to just the "intercranial" space). By doing so, it extends all the way up to just a millimeter or two below the skin. Furthermore, with a high-profile configuration, it becomes easier to palpate with digital exam so as to assist the healthcare workers in feeling around the temporal skin for the circular diaphragm set up to receive percutaneous medicine injection. The new temporal implant design (combining hard and soft tissue) encompasses outward from the skull space and extends outward into the normal temporal muscle space, the normal temporal fat space, and the normal subcutaneous space. This configuration increases several-fold the volume available for multi-purpose, embedded technologies for brain medicine delivery. Furthermore, an improved anatomical location such as this, with a novel position of anatomy-specific, pre-fabricated devices within both the cranial bone space and overlying soft tissue area like temporalis muscle and temporal fat, presents a new-found strategy for enhanced medicine delivery of rechargeable battery-powered platforms capable of local neurological medicine delivery would be a welcome addition to the art. For example, with more space, the possible of having larger rechargeable battery platforms comes to life. And because of this volume increase, the patient's charge cycle can switch instantly from needing a 1 hour charge three times a day (i.e., every 8 hours) to needing a 1 hour charge every three days—which is a major difference for the neurosurgical patient receiving localized brain medicine delivery and drastically changes the risk of non-compliance (i.e., more room inside equates to better accommodation for larger battery sizes). Also, the advance here is utilization of the combined hard and soft tissue space for embedded technologies within a pre-fabricated implant made by way of anatomical-averaged, CAD/CAM design—so that when a patient presents with an unexpected brain tumor and new onset seizures, there isn't a wait of several days or weeks to customize the implant design. The present invention can allow hospitals to stock anatomy-specific temporal implants for combined soft and hard tissue reconstruction on the shelves, a brain tumor patient undergoing tumor resection and craniotomy could have this implant placed in one surgery—instead of two surgeries. For instance, the temporal fossa and the temporal soft tissue normally average 22 to 24 cubic centimeters (as published by the present inventor in his article entitled "Quantitative analysis of dual-purpose, patient-specific craniofacial implants for correction of temporal deformity" *Neurosurgery* 2015 PMID 25710104), and thus, the present inventor has leveraged his clinical expertise and knowledge base to design a multi-purpose anatomy-specific device to fit snugly within this alluded space; consequently, the implant of the present invention may have about 65-70 cubic centimeters of volume, which is nearly two or three times as much volume when using only the cranial bone space. In addition, the anatomical placement of this technology above the skull—as opposed to being limited to within the skull—is both advantageous for the device engineer looking to include within many different components, easier to fill with a transcutaneous needle (given that the top edge extends upward to the skin as opposed to staying deeper at the bone level), and less invasive and easier for the surgeon to implant. Consequently, the functional component may be considered "high-profile", in that it has at least a portion thereof extending outwardly from the bone level towards the skin, or, in other words, above the skull. Similarly, local medicine delivery requires that the refillable diaphragm be snugly positioned just under the skin for easy needle penetration, and that means that placing the device within the soft tissue space is advantageous in comparison to only placing the device within the skull and having a thick scalp above (i.e., a thick scalp with bacteria-laden hair would interfere with the needle penetration system which is critical in allowing monthly refills of neurologic medicines for chronic brain disease management). In parallel, the present invention may further be applied to tumor areas other than just the brain. For example, the device of the present invention may be positioned above the chest/ribs and utilize the bone (hard tissue) and pectoralis muscle (soft tissue) combined tissue space to be safely maintained in a place that allows for pump-assisted medicine delivery to the lung for instances needing chronic pump-assisted infusion like lung cancer or chronic infection like pneumonia. Similarly, the present invention could also be positioned along the lower bony ribs and rectus abdominus muscle (as a combined hard and soft tissue space) to allow placement for solid organ cancer chronic infusion, for example in case of liver cancer or hepatitis treatment. Yet another combined hard and soft tissue area may include the spine (hard) and paraspinous muscles (soft) as a combined space for device placement allowing direct, pump-assisted medicine delivery for the spine (i.e., anti-pain, anti-tumor) and/or orthopedic joint areas like the hip, knee, shoulder and ankle for chronic pain medicine infusion or cancer. Thus, a concept of using the bone and soft tissue space for local brain medicine delivery via convection-enhanced pump mechanisms could be translated over to other anatomical areas requiring combined hard and soft tissue reconstruction and localized medicine delivery. Again, the limits of strict bone replacement (as previously described by the present inventor in U.S. Pat. No. 11,058,541, entitled "Low-profile Intercranial Device" and in published application WO-20200006240, entitled "Magnetic resonance imaging compatible, convection-enhanced delivery cranial implant devise and related methods") present further challenges of confined space during design, and thus limits both the amount of stored medicine within, the space for embedded wireless charging technology and battery storage, and the size dedicated to pump-assisted technology. By expanding the implant design and its footprint within the human skull and extending outside the normal bone boundary to include the neighboring temporalis muscle, temporal fat and temporal subcutaneous tissue, more room for brain medicine delivery is available, which would equate to less periodic fills needed (more room for long-term medicine storage and larger reservoir), more room inside allows for a larger energy storage platform via RF charging, safer wireless battery charging (i.e., an implant with an extension closer to the skin level means less tissue interference with regards to the embedded, wireless charging mechanism), and better patient satisfaction.

For example, during brain tumor craniotomy surgery for recurrent glioblastoma disease and need for repeated resection, one would be challenged in placing a standard MRI-compatible device within the head. This is because any device within a brain tumor patient must not just be MRI-safe and/or MRI-compatible (defined as absent ferrous-containing material), but more importantly, it should be considered MRI-lucent, distinct from being merely MRI-safe and MRI-compatible. As used herein, "MRI-lucent" means that the device can sit within the temporal fossa, in a combined space of hard and soft tissue just a few centimeters away from the brain and the previous brain tumor location, and be relatively invisible (i.e., radio-lucent) to the MRI machine in charge with identifying brain tumor recurrence on periodic scans every 3-4 months, (i.e., the present invention provides zero radiologic artifact). The present inventor has posited that, to a malignant brain tumor patient for whom is getting monitored every 90-120 days for brain tumor recurrence, it is imperative that their combined, multi-purpose device is not only MRI-compatible in design, but is also MRI-lucent. For example, in PCT application PCT/US2019/039519, entitled "Magnetic resonance imaging compatible, convection enhanced delivery cranial implant devices and related methods", the present inventor described the implant being MRI-compatible. However, for the present invention, the device within the combined soft and hard tissue space is not merely MRI-compatible, but is rather enhanced in its design so as to be MRI-lucent"— which is a major advance for neurosurgical patients with chronic brain disease requiring meticulous MRI surveillance, such as with glioblastoma and malignant brain tumors. This may be accomplished by avoiding the use of electroactive polymers, and to instead use an electro-osmotic pump full of simple water (or equivalent). Hence, it's the electroactive polymers (EAPs) that may cause artifacts and thereby inhibit proper monitoring of the brain tumor patient receiving chronic medicine delivery. Additionally, in the aforementioned application, the present inventor described placing the device within the skull space, which he has now determined as being too limiting when it comes to building pump-assisted devices for brain medicine delivery and bypassing the blood-brain barrier. In contrast, the present invention remedies the deficiencies of the present inventor's prior patents and patent applications that are described herein. One, the device of the present invention is non-patient specific, and instead anatomy-specific. Second, the device of the present invention does not need to stay within the skull space like a L.I.D., and instead is placed within a combined anatomical space incorporating both cranial muscle/fat and cranial bone—thereby allowing the engineers much improved volumes for pump-assisted technology within. With this additional space, the engineering team can use non-ferrous materials unlike before when working in space-limited implants occupying the cranial bone space. The engineers are now removed from design constraints and much more successful in building device components absent of any iron and/or artifact-causing materials. Third, the device of the present invention includes an MRI-lucent design which removes radiographic artifacts altogether, and instead uses an electro-osmotic pump (or equivalent) rather than an electroactive polymer (i.e., replacing MRI-opaque gels with MRI-lucent water).

The present invention may also find applications in chronic neurological disease states like neurodegenerative disease (i.e., Alzheimer's, Parkinson's), medicine-resistant epilepsy, neurotrauma/paralysis, major depression, schizophrenia, bipolar disease, ADHD in children, brain dysfunction (i.e., paralysis), brain related age-changes (i.e., memory loss), and post-traumatic stress disorder. Also, future options may include stem cell injections via this device for enhanced brain recovery following traumatic brain injury, cancer or stroke, as well as brain-enhancing medicines or supplements that could increase one's memory, athletic performance, balance, hand-eye coordination, brain-computer interface, and/or high-stress situation performance (military, police, etc.)

For placement, the surgeon may remove any and all diseased or damaged portions of the skull (craniectomy defects), or may electively remove normal bone to make room, while the brain is exposed underneath without injury. In addition, as the normal temporalis muscle and temporalis fat shrinks after previous craniotomy (i.e., post-craniotomy temporal soft tissue hollowing), there will be extra volume in which the device of the present invention can be placed— as opposed to the normal, pre-operative volume of the muscle and fat. Therefore, a combined hard and soft tissue reconstruction temporal implant with medicine delivery capabilities can facilitate bypassing the blood-brain barrier, and further, due to its design and reconstructive aspect, can restore the soft tissue volume back to its pre-operative state. This phenomenon of "soft tissue temporal hollowing" is related to deinnervation and/or devascularization of the temporal soft tissue during standard pterional craniotomy for a brain tumor. Hence, when the surgeon comes back for revision surgery, the muscle and fat need some type of implant reconstruction (i.e., augmentation), wherein the device of the present invention may be used. The present device not only provides more internal volume, but also serves as a reconstructive option for brain surgery patients wishing to correct and/or prevent temporal hollowing deformity. Following resection of this diseased cranial bone (either in a "multi-staged" fashion with one surgery completed ahead of time for bone removal prior to implant placement, or in a "single-stage" fashion where the implant is placed at the same time of removal), such craniectomy defects are often reconstructed with custom craniofacial implants (CCIs)—as opposed to using generic, "off-the-shelf" materials which currently fail to provide any true anatomical replacement. Historically, however, cranioplasty patients requesting CCI-based reconstruction for an ideal appearance were limited to "second-stage" operations in instances of pre-existing skull defects so that the exact fit and design could be obtained. However, recent modifications by the present inventor have revolutionized the field of skull replacement surgery and is termed "single-stage cranioplasties"—by which a clinician, such as a neuroplastic surgeon or neurosurgeon, manually reshapes/resizes a previously-ordered, custom implant (with oversized dimensions) to fit perfectly into the skull defect as true anatomical replacement—as opposed to using an "off-the shelf" material for which only partially restores the missing bone. Either way, for single-stage methods involving skull tumors or second-stage cranioplasties for pre-defined skull defects, the advent of computer-aided design/manufacturing (CAD/CAM), has provided surgeons alike with perfectly-shaped CCIs designed and manufactured based in part on fine cut preoperative computed tomography (CT) scans and three-dimensional reconstruction (+/−stereolithographic models). However, present day challenges do not limit themselves to just missing cranial bone. A new invention is now needed to use CAD/CAM designing for anatomy-specific implants capable of replacing both hard (bone) and soft tissue (overlying muscle and fat), given that the present inventors advance of embedded technologies requires a larger footprint (i.e., to fit Bluetooth modules, wireless RF charging units, microprocessors, MRI-lucent pump technology, real-time biosensors, imaging arrays with ultrasound crystals, etc.) and docking station to truly advance the field. Such temporal devices may have wireless charging platforms developed to be fully MRI-safe, in specific areas like charging with radio-frequency (RF) signals instead of the standard, MRI-adverse, magnetic coils used in commonly found household devices and cellphones. Such multi-purpose devices may also have a Bluetooth, wireless connection and enhanced security design with extensive threat modeling to prevent biohacking and abnormal medicine delivery rates. Such devices may also have within a computer chip and internal processor to help self-guide ideal flowing of the pump-assisted mechanism. Such devices may have a small computer chip capable of constant monitoring a flow rates through each of the 4-5 catheters pumping medicine into the brain, so as to self-detect, overcome, and accommodate unexpected scar tissue or increased resistance to flow in any one or more catheters at any time. Such a novel constant monitoring mechanism disposed within the temporal implants so that each catheter pumping medicine into the brain can continue a steady flow around 0.5-1.0 microliters/minute, regardless of how much resistance is located at the catheter-brain interface. Scar tissue, radiation changes, and/or recurrent brain tumor disease can all negatively affect the flow rates exiting each of the embedded catheters. Hence, the newfound extra space within this hard and soft tissue implant now allows the engineers to incorporate additional safety mechanisms such as "cruise-control flow rates" by embedding several biosensors along the fluid circuit. Such devices may also have remote biosensors to detect abnormal fluid accumulation around the brain requiring immediate medical attention and mobile messaging. For instance, the normal intracranial pressure is around 5-15 mmHg, and so any increased pressures from fluid extravasation or implant malfunction requires immediate detection; with the additional space herein, the extra technology has room to now be incorporated. Such devices may also have miniature ultrasound arrays housed within the bottom of the device, facing the brain, that may use artificial intelligence to self-monitor the brain tumor cavity for any growth changes related to recurrent tumor and/or irradiation-induced scar tissue. Such devices may also have a palpable, "high-profile", diaphragm located just a millimeter or two below the temporal scalp's skin, as a safer entry point capable of around 1000 repeated transcutaneous needle sticks (through the scalp) using a special non-boring needle and material design preventing any type of accidental leakage (especially since the filling of chemotherapy is very dangerous and caustic to the surrounding skin). Such devices may have a small computer chip capable of "cruise-control" to allow constant monitoring a flow rates through each of the 4-5 catheters pumping medicine into the brain, so as to self-detect, overcome, and accommodate unexpected scar tissue or increased resistance to flow in any one or more catheters at any time. Such devices may have a mobile app capable of sending real-time, patient-protected data to the patient, patient's family, and/or patient's healthcare providers—with critical information such as medicine storage amounts, data with respect to flow rates, etc. Such devices may also one day have internal suction capabilities in that they can self-withdraw fluid from the diseased brain along with cells for biopsy and diagnosis, all of which can be accessed via a small subcutaneous port—simply by reversing the flow of the MRI-lucent pumps.

As discussed herein, prior inventions by the present inventor were only limited to the bone space; currently, recent investigations by the present inventor reveal that components like MRI-lucent batteries, computer chips, catheters, biosensors, pumps, Bluetooth modules, RF charging components, radio antennas, etc., all require more three-dimensional space prior to the present inventor's original concepts. As such, one needs to advance the field by pre-fabricating combined soft and hard tissue temporal implants with bigger footprints to house powerful, life-changing technologies unlike ever before. Thus, the field of solid bone replacement for neuroplastic surgery, neurosurgery, neuro-oncology and craniofacial surgery could greatly be improved by changing the design confines to include some of the surrounding soft tissue (i.e., temporalis muscle, temporal fat pad, and temporal scalp subcutaneous tissue), to provide an additional footprint for the use of embedded technology like biosensors, medicine delivery, or remote imaging within multipurpose, anatomy-specific implants.

In parallel to skull replacement, joint replacement by orthopedic surgery since the 1960's has also enjoyed overwhelming success by replacing bone defects with disease such as osteoarthritis and cancer in a way that forever improved restoration of form and function. However, orthopedic-style implants are only designed to replace bone like joints involving the hip, knee, shoulder and ankle. No consideration has been given to capitalizing on the surrounding soft tissue space—either in orthopedic surgery or in this implantable neurotechnology space. Furthermore, these bone-only implants (both off-the-shelf and pre-fabricated) are solid inside with no embedded function. Thus, the field of solid bone replacement for orthopedic joint surgery could greatly be improved by changing the design confines to include some of the surrounding soft tissue, to provide an additional footprint for the use of embedded technology like biosensors, medicine delivery, and/or remote imaging.

In parallel to skull replacement, spine surgery for various diseases like trauma, paralysis and/or cancer have experienced much success using hard-tissue implants designed for missing vertebrae (bone elements of the spine). However, spine surgery-style implants are only designed to replace bone-like structures like the vertebrae and/or pelvis. No consideration has been given to utilizing the surrounding soft tissue space—like the paraspinous muscle, which is quite similar to the temporalis muscle in this regard. Furthermore, these bone-only implants (both off-the-shelf and pre-fabricated) are solid inside with no embedded function. Thus, the field of solid bone replacement for spine surgery could greatly be improved by changing the design confines to include some of the surrounding soft tissue, to provide an additional footprint for the use of embedded technology like biosensors, medicine delivery, Bluetooth connectivity, wireless charging, and/or remote imaging.

In fact, recent journal publications suggest that the use of CCIs designed by the present inventor with dual-purpose ("Zhong S, Huang G J, Susarla S M, Swanson E W, Huang J, Gordon C R. Quantitative Analysis of Dual-Purpose, Patient-Specific Craniofacial Implants for Correction of Temporal Deformity. *Neurosurgery* 2015 June; 11(1):220-9) can better preserve post-neurosurgery appearance, prevent post-operative deformity with accompanying social stigma, decrease total operative times, prevent scalp-related wound complications, and enhance patient satisfaction—and therefore, they serve as an ideal medium for reconstructing neurosurgery patients. This major advance was accomplished by using a novel design algorithm provided by the present inventor which capitalized on the under-utilized hard and soft tissue space around the brain (thereby erasing the old, outdated, generational dogma that cranial implants could and should designed for the anatomical bone space only)—and how this new advance could be reliably accomplished using pre-operative, CAD/CAM design. However, at the time, there was no computer-aided surgery technology available to guide the surgeon in performing "single-stage bone replacement of the skull", other than by hand-carving the implant intra-operatively with simple eye-hand coordination and common-day burring. Thus, the present inventor worked diligently to design and invent a technology to provide the surgeon real-time, computer-guided information for streamlined size modification. Hence, in U.S. Pat. No. 10,448,956, entitled "Computer-Assisted Planning and Execution System" and U.S. Pat. No. 10,603,175, entitled "Cutting Machine for Resizing Raw Implants During Surgery", the present inventor described a recently-developed surgical workstation with the novel ability to provide intra-operative visual guidance related to planned-versus-actual position of CCI (on intraoperative visual monitors)—following placement of the CCI within the three-dimensional craniofacial defect (in relation to virtual plan)—which ultimately adds even greater precision and simplicity to this complex operation. Notably, this CCI-related technology—both computer-assisted and robot-assisted—could be employed for just bone-replacement design or combined hard/soft tissue, dual-purpose design. Regardless, all CCIs up until recently were used to replace abnormal bone having some form of disease, either of benign or malignant etiology. Thus, these customized skull implants were termed "static CCIs" (SCCIs)—mainly because their main constant purpose (i.e., unchanged purpose with respect to time) encompasses strictly two benefits following placement—"brain protection" and "enhanced appearance". Therefore, in the past, the present inventor described a novel solution to "static" or "non-functioning" implants for bone replacement—as way to improve the field—by way of introducing the Low-profile Intercranial Device (L.I.D.), which describes strictly bone replacement with embedded technologies (mainly the cranium). There, the term "intercranial" was used, so as to illustrate the technology being confined to the bone-only space. However, the present inventor's recent efforts have shown this to be disruptive and rate-limiting when it comes to achieving successful chronic brain medicine delivery to help bypass the blood-brain barrier. Now, the present day inventor is advancing the field further by describing the limitations of "static" or "non-functioning" patient-specific and anatomy-specific craniofacial implants with dual-purpose design—replacing combined hard and soft tissue defects, and by drastically extending the confines of their design away from "intercranial" and towards "extracranial" instead. Hence, the present invention is directed towards multi-purpose, anatomy-specific implants for combined hard and soft tissue reconstruction with embedded technologies for improving form and function.

Meanwhile, there are many FDA-approved, "off the shelf" technologies that have life-changing or life-saving functionality. Specifically, in neurosurgery, there are technologies capable of delivering electrical impulses (i.e., epilepsy management), pumping neurological medicines (i.e., chronic pain), or syphoning/diverting excess cerebrospinal fluid with programmable shunt valves (i.e., hydrocephalus management), but aren't customizable or designed to protect the brain. However, each of these neurotechnology implants—supplying intermittent or ongoing interaction with the central nervous system in some capacity—have a large, irregular footprint and suboptimal shape design incompatible with the principles of neuroplastic surgery—whose mission is to optimize both form and function. Similarly, the same exact design setbacks could be said for revolutionary technologies in orthopedic and spine surgery. Many revolutionary technologies are placed in patients with chronic pain, debilitating disease and/or tumor disease along the spine, pelvis, and joints, but the design flaws accompanying these technologies leads to visual deformities and high-rates of extrusion due to the incompatible shapes and failure to respect to the anatomical boundaries of the overlying soft tissue (i.e., muscle/fat). Again, such embedded neurological implants do not fall into the normal anatomical barriers of the scalp or skull and therefore cause risk by impinging neighboring tissues and visual deformity. If the implant is above the skull and poorly shaped, then it equates into premature extrusion and premature removal. If the implant is bulky and placed under the skull, it equates to cortex impingement and focal symptoms related to brain impingement. Thus, for the field of implantology and embedded technologies to greatly advance together, the present invention may 1) incorporate hard and soft tissue boundaries into both pre-customized and non-customized, anatomical-specific, designs and 2) by adding additional soft tissue space into the bony implant CAD/CAM designing, subsequently provide the embedded technology more room (i.e., severalfold) for encapsulation and long-term safety. As such, modern day neurologic devices (brain, spine and orthopedic implants alike) will no longer be confronted and challenged with high extrusion and infection risk (i.e., current flaws in modern day devices leads to high incidence of pain and extrusion through overlying skin thereby requiring premature explantation) approaching an incidence of roughly 50%. Similarly, battery-powered, low-profile devices for intercranial placement within specific anatomic tissue planes along the bone space only were subsequently described in the present inventor's issued patent directed towards low-profile intercranial devices (LIDs). In parallel, the fields of neurosurgery, neuroplastic surgery, and orthopedic surgery have been hampered and limited in many critical areas needing improved implant delivery, including examples like battery-powered neuromodulation/cortical stimulation for epilepsy/movement disorders, valve-devices for hydrocephalic disease, pump-assisted local delivery of neurological medicines for brain tumors, revolutionary spine implants for spinal cord injury monitoring/treatment, and chronic pain related to joint osteoarthritis. One of the reasons being that the bone space—and current day implant design—is not always big enough to accommodate the life-changing, life-enhancing, or life-saving technology modalities and so extrusion, infection, and pain are staggering high thereby limiting successful outcomes—and hence, a new invention with a much larger footprint—and one that is anatomically-sensitive by respecting the boundaries of the normal soft tissue envelope—is unquestionably needed. For instance, the novel pump-assisted design incorporating electro-osmotic contents, Bluetooth chips, integrated biosensors, RF charging platforms, and refillable medicine reservoirs, for are all now capable of being purely MRI-lucent, together require a significant footprint and one that is not compatible with bone-only designs.

Additionally, there is a long-sought need for a two-piece, multi-purpose, anatomic specific implant. The first purpose of such a device is to restore rigidity and structural integrity to the missing or replaced bone. In reverse, having a weak, soft outer case would be dangerous for the brain surgery patient. Next, such a device may replace the missing volume of hard and soft tissue to correct and/or prevent visible contour deformity. In addition, by extending up past the bone boundary and up closer to the skin, such a device may allow the Bluetooth module/wireless charging battery to have less soft tissue interference and/or allow the refillable reservoir to be less deep from the skin surface and therefore easier for the doctor or nurse to fill the refillable medicine chamber with a special non-boring needle. Lastly, such a device with "high-profile contour" may utilize the enlarged neighboring spaces of hard and soft tissue to provide the field a novel solution given that there is less tissue obstruction to the outside world, which is critically important when it comes to wireless technology. Furthermore, the design of such a device can be uniquely enhanced in future iterations by offering the surgeons an integrated or independent soft tissue implant component adapted to replace or restore missing soft tissue in "plug-and-play" fashion as many patients age with chronic disease, that may often change with respect to time. Of note, this approach is different from the previous inventions described by the present inventor related to patient-specific craniofacial implants (U.S. Pat. No. 10,639,158). In contrast to those, the soft tissue implant component can now be physically adapted and coupled—in a way analogous to interdigitation of a lock and key, thereby preventing micromotion and/or leakage of fluid—to a rigid base component replacing the resected or missing bone (i.e., cranial bone, spine/vertebral bone, and joint bone). For example, this would be helpful in brain tumor patients for whom need to switch over to a different chemotherapy drug as the cancer changes its cellular composition and aggressiveness for recurrence. Thus, the rigid base component thereby includes a skull, spine or orthopedic joint implant adapted to replace missing bone or healthy bone for which needs removal and immediate (i.e., "single-stage reconstruction"). Again, the hard tissue component with the skull—housing the catheters extending downward into the brain—would not need to be moved or changed, thereby increasing the safety of the procedure. The novel, "plug-on" soft tissue implant is designed pre-operatively on standard anatomical averaging or with CAD/CAM design concentrating on the anatomical boundaries of the overlying soft tissue, which, in both instances, provides newly discovered volume to include embedded technologies of various function for which may provide life-enhancing, life-changing, and/or life-saving drug delivery modalities unlike before. Another application of this unique "plug-in" design could be the switching out of a non-functioning battery or component. Specifically, the soft tissue implant component may be interchangeable with another soft tissue implant component in plug-and-play fashion to allow rapid changing of medicine reservoirs or biosensing or imaging hardware or rechargeable batteries, if and when the previous therapy is no longer needed. For instance, neuromedicine containers having a standardized shape may be provided, allowing for a "plug-and-play" design facilitating easy replacement of the container, and allowing the functional component to be medicine-agnostic.

But with increasing experience popularized by the present inventor and now surgical complication rates exceedingly low, CCIs are being more often modified in real-time for scenarios where more or less skull bone is removed and the skull defect dimensions do not match up perfectly to the pre-fabricated CCI (versus an originally envisioned, for example, as designed in a planning stage)—including such associated methods of making the CCIs are described in U.S. Pat. No. 10,603,175, entitled "A Cutting Machine For Resizing Raw Implants During Surgery" employing robot-assisted technology, U.S. Pat. No. 10,835,379, entitled "Method for Performing Single-Stage Cranioplasty Reconstruction with a Clear Custom Cranial Implant" employing a translucent color and enhanced visibility for on-table manipulation and tracing over irregularly-shaped skull defect, and U.S. Pat. No. 10,448,956, entitled "Computer-Assisted Planning and Execution System" employing computer-assisted technology to modify and enhance placement of the skull implant with intra-operative navigation. Of note, the present inventor recently introduced single-stage cranial implant reconstruction by way of clear-colored, translucent implants—thereby allowing an ability to see through the implant in real-time as a way to minimize challenges associated with marker pen tracing. However, this clear-colored cranial implant was only described as replacing missing cranial bone. Hence, the field of reconstructive surgery needs a clear-colored implant for which replaces both hard (i.e., cranial bone) and soft tissue (i.e., muscle/fat) anatomies for the purpose of embedding technologies within. Similarly, the present inventor described using a clear-colored implant to fabricate the device described in U.S. Pat. No. 11,058,541, entitled "Low-profile Intercranial device". However, again, this device was conceived to only fill the "intercranial" space and failed to include design alterations and strategies to successfully include a combined hard and soft tissue replacement strategy for chronic brain medicine delivery. Hence, the field needs a clear cranial implant with "extracranial" design and one with a "high-profile extension" so as to allow easy, safe percutaneous needle entry (versus a "low-profile" design which impairs utility with respect to medicine delivery and user palpability of the skin-covered access point).

Due to the recent reductions for time needed to design, fabricate and implant CCIs, more cranioplasty procedures with alloplastic implants are being performed around the world than ever before—but the limiting factor is that they strictly replace missing bone that can be pre-defined on pre-operative imaging. Until most recently, these cranial implants were opaque in color and provided the surgeon zero visibility to the brain and surrounding structures underneath. The present inventor thus spent significant effort in developing both computer-assisted (U.S. Pat. No. 10,448,956 "Computer-Assisted Planning and Execution System") and robot-assisted technologies (U.S. Pat. No. 10,603,175 "A Cutting Machine for Resizing Raw Implants During Surgery") to help circumvent these obstructive limitations and labor-intense efforts accompanying intra-operative size modification of opaque-colored bone-replacement implants. Accordingly, these recent developments in CCI sterility, shape design, and streamline production, and color—together provide an opportunity that extends CCI-based cranioplasty beyond only patients who require replacement of pre-existing craniectomy defects. Notably, recent advances by the present inventor now show that opaque-colored cases may be preferable for medicine-delivery devices versus those that are clear-colored. For example, from a sales perspective, a company may prefer that the surgeon customer base not be able to see all components inside, and thus, having an opaque case may have a strategic business advantage. In addition, certain design elements within may be altered with respect to visible light, and hence a clear-colored case could be detrimental to long-term function. Therefore, what is needed in the art, are new pre-fabricated, anatomy-specific and/or customized implantable devices with high-profile contours which replace both hard and soft tissue simultaneously (i.e., to avoid soft tissue-related complications and high extrusion risk leading to premature explanation like in joint surgery, spine surgery, and neurocranial surgery). What is also needed in the art are corresponding methods of making and implanting such implant devices, including methods using computer-assisted and/or robot-assisted surgical procedures, as described by the present inventor. For instance, placement of these combined soft and hard tissue reconstructive implants within the human skeleton could be better enhanced by way of robotic platforms and/or computer-guidance, as well as the outwardly extending portions such as brain-implanted catheters for medicine delivery. Such improvements would exploit the benefits of direct access to the brain, spinal cord, or joint area and ideal anatomical location/proximity provided by these novel CCIs—being placed directly on top and just a few millimeters away from the central nervous system (brain and spinal cord) and critical nerve structures (various joint locations like shoulder, hip, knee and ankle) to deliver life-changing interventions provide an unprecedented method to deliver locally. For example, robotic and computer-assisted technologies would enhance hard and soft tissue placement of neurologic deep brain stimulators, neurologic medicine delivery systems such as presented here, neuromodulation devices, imaging devices, radiation therapy devices, and remote sensing/monitoring devices. Again, by adding a soft tissue extension to each bone implant design, the field now experiences a much overdue supply of additional volume to work with, and one that is safe since it follows the soft tissue anatomical limits found on pre-operative imaging like CT scanning or MR imaging (particularly, soft tissue windows). This is a much-improved approach, as opposed to placing similar functional devices either above or below skull, spinal vertebrae, or bony joint in non-anatomical locations, which is the standard, suboptimal method employed currently by neurosurgeons and orthopedic surgeons alike. Furthermore, the present inventor's U.S. Pat. No. 11,058,541, issued Jul. 13, 2021 and entitled "Low-profile Intercranial Device", the disclosure of which is incorporated herein by reference in its entirety, provided improvement in using the pre-defined anatomical boundaries of the cranial bone only to design customized implants (hence, the use of the adjective "intercranial"). Embodiments of the present invention, however, use a further improved design and shape by incorporating the implant to also fill-in the overlying soft tissue (i.e., "extracranial"—either as a dual-purpose, anatomy-specific implant replacing bone and soft tissue, or as an isolated implant only filling in soft tissue (for isolated cases where the bone defect is small, non-existent due to disease, or not needed secondary to consolidated footprint size). Lastly, both the central and peripheral nervous system is encased by bone along the skull, spine, and joint spaces—as well as hearty soft tissue in the scalp, back and surrounding joint areas. Therefore, such a multi-purpose, anatomy-specific implant would further optimize its utility, safety, design constraints, and ultimate placement by a novel way of utilizing newfound soft tissue space abutting the bone. Furthermore, a two-piece design (whether fused virtually and fabricated as a single implant, or created as two-pieces and fitted together intraoperatively by the surgeon) allows the outer piece to employ a "plug-and-play" type arrangement for neurosurgical/orthopedic patients who need a different functional device housed withing their head or spine or joint space—one that could easily switch out depleted medicine reservoirs/batteries/components or those where the type of medicine/battery needs to be changed, full memory chips no longer capable of capturing biosensor or imaging data, and the like. Thus, a first part employing the bone space may remain constant, while a second part employing the soft tissue space may be exchanged and altered as desired by minor surgery. By having an interchangeable soft tissue component, the procedure to switch out "soft tissue implants" becomes much less invasive and better tolerated by each patient—given that removal of cranial bone in the head requires a craniotomy with risk of stroke/bleeding/seizure and highly-invasive surgery, removing bone along the spinal column or joint space requires complex spine/limb surgery with risk of paralysis, decreased mobility, pain, etc. Hence, it is in the best interests of both the patient and the surgeon to leave the hard-tissue component undisturbed, and to only switch out the soft tissue component when and if indicated.

SUMMARY

According to at least one exemplary embodiment, a high-profile, anatomy-specific craniofacial implant for combined hard and soft tissue reconstruction with embedded technology for medicine delivery is disclosed. The implant may be adapted to fill hard and soft tissue space within the temporal area. The embodiments disclosed within can include an extended "high-profile", soft tissue component, having disposed therein a functional component having at least one catheter for delivery of medicine to the brain. The implants of the embodiments disclosed herein may be non-patient-customized, but rather anatomy-specific, and may designed, for example, by CAD/CAM or non-customized, anatomical averaging design. The functional component may be disposed in the soft tissue component, thereby utilizing the overlying soft tissue space, for direct, chronic, pump-assisted, multiphase medicine delivery to the brain by bypassing the blood-brain barrier. Additionally, the soft tissue implant component adapted to replace or restore missing soft tissue may be replaceable or interchangeable in a "plug-and-play" fashion. Accordingly, the soft tissue implant component may be adapted to be coupled by a lock-and-key connection to a rigid component replacing the resected or missing bone. The functional component may further have a refillable reservoir having a diaphragm capable of repeated penetration by needles through the skin above or Bluetooth module/battery platform extending up to just underneath the skin. The rigid component can be a skull, spine or orthopedic joint implant adapted to replace missing bone, or healthy bone which needs removal and immediate, "single-stage reconstruction". The soft tissue implant may include embedded neurotechnologies of various function for which provide life-enhancing, life-changing, and/or life-saving modalities. The soft tissue implant component may be interchangeable with another soft tissue implant component in plug-and-play fashion if and when the previous technology is no longer needed.

BRIEF DESCRIPTION OF THE FIGURES

Advantages of embodiments of the present invention will be apparent from the following detailed description of the exemplary embodiments. The following detailed description should be considered in conjunction with the accompanying figures in which.

DETAILED DESCRIPTION

Figure 1:
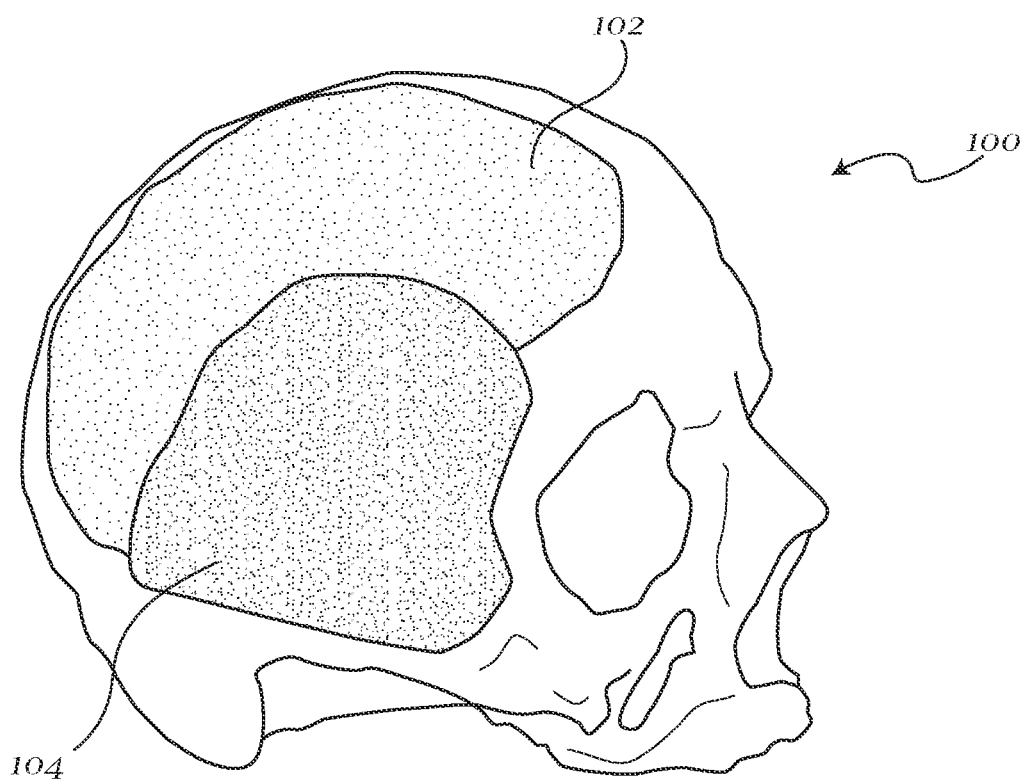
FIG. 1 shows a first exemplary embodiment of a multi-purpose implant, applicable to the cranium.

Aspects of the invention are disclosed in the following description and related drawings directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Furthermore, the present application refers to technologies developed by the present inventor and disclosed in U.S. Pat. No. 10,639,158, issued May 5, 2020 and entitled "Patient-specific craniofacial implants" and U.S. Pat. No. 11,058,541, issued Jul. 13, 2021 and entitled "Low-profile Intercranial Device" and "Magnetic resonance imaging compatible, convection-enhanced delivery cranial implant devise and related methods" [published, WO-20200006240-A1], the disclosures of which are incorporated herein in their entireties. As used herein, a "multi-purpose implant" may refer to an implant adapted to perform one or more of: protecting the brain or spine; restoring or preventing deformity; and providing anatomically-specific housing for embedded neurotechnologies, and more importantly, is not limited to the "intercranial" space.

Cranial Embodiments

The act of brain surgery most often requires a craniotomy of significant size. The majority (approximately 75%) of all craniotomies are done within the pterional region. Thus, the temporal anatomy may become distorted due to devascularization and deinnervation of the critical structures such as the temporalis muscle and temporal fat pad (i.e., pertinent soft tissue). As such, facial symmetry may be forever jeopardized and distorted following the breach of this anatomy. In addition, a significant number of neurosurgical patients may lose the bone flap (i.e., the segment of bone removed for access to the brain) due to either infection, tumor involvement, brain swelling, and/or traumatic fracture. Therefore, a second surgery is required, known as cranioplasty, to reconstruct the missing cranial bone. Similarly, the act of spine surgery requires removal of some bone in order to access the spinal cord (i.e., laminectomy), which can also suffer from bone-related issues and needs improvement. For both the cranium and spine, the art and science of manmade alloplastic implants arose in the 1990's but solely concentrated on replacing the missing bone with patient-specific design. The present inventor had previously invented the first description of patient-specific craniofacial implants (described in U.S. Pat. No. 10,639,158, incorporated herein in its entirety) to replace the missing soft tissue at the same time of skull reconstruction, by employing novel computer-assisted design algorithms concentrating on the above soft tissue. Most recently, the present inventor had invented an improved design for which involves better-defined anatomical vector lines for improved consistency (i.e., enhanced results), a pre-fabricated temporal window to prevent soft tissue impingement at time of placement, and the first-ever description of placing these craniofacial implants above the scarred-down temporalis muscle as opposed to underneath it. However, the surgeon is limited in these inventions by the fact that these "dual-purpose craniofacial implants" (wherein the first purpose is to replace missing bone for brain protection and the second purpose is to restore facial symmetry secondary to soft tissue deformity) are delivered as one larger implant, as disclosed in Zhong et al., "Quantitative Analysis of Dual-Purpose, Patient-Specific Craniofacial Implants for Correction of Corporal Deformity", the disclosure of which is incorporated herein in its entirety.

First Embodiment

Figure 2:
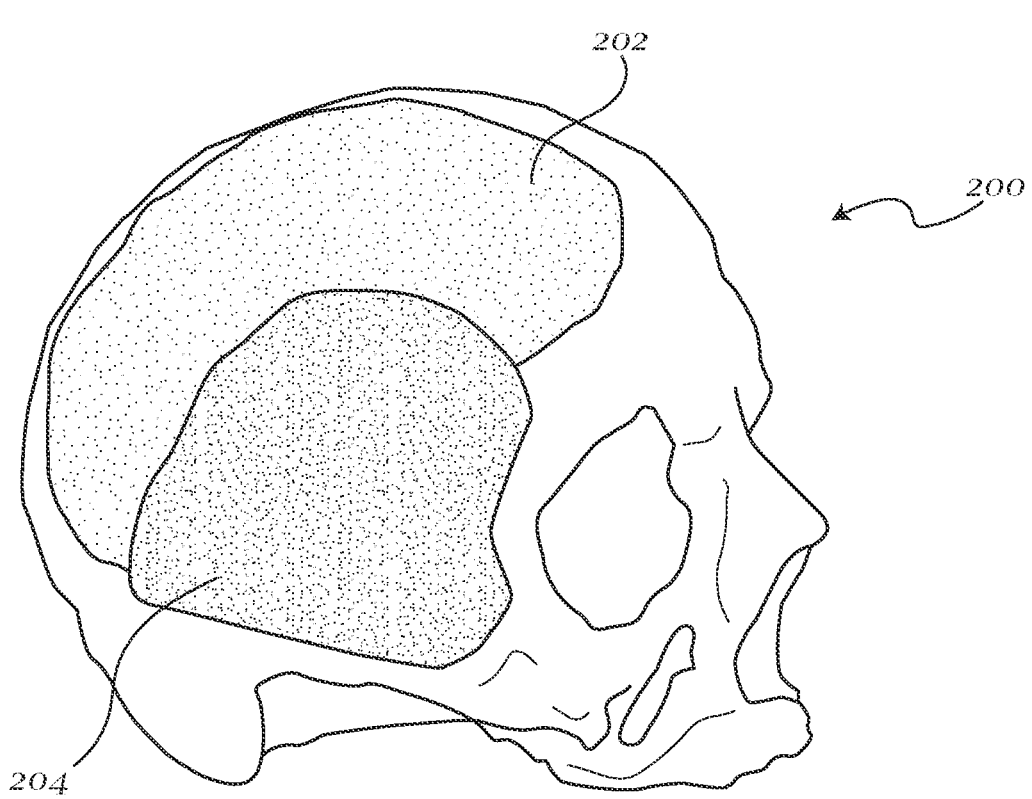
FIG. 2 shows a second exemplary embodiment of a multi-purpose implant, applicable to the cranium.

As shown in FIG. 1, a first exemplary embodiment 100 offers the surgeon a two-piece design with a standard cranial bone replacement implant 102, along with a small-, medium-, and large-sized soft tissue implant component 104—which the surgeon can decide to use at time of cranioplasty based on intraoperative assessment and degree of soft tissue resorption. In the first exemplary embodiment 100, anatomy-specific craniofacial implants can be delivered as two separate implants following virtual fusion/shape creation by way of CT scanning and CAD/CAM design including: a) a skull implant 102 designed to replace missing cranial bone (i.e., pre-existing skull defect); and b) a soft tissue implant 104 designed to replace missing temporalis muscle/fat wherein the fabrication process provides two implants to the surgeon and a lock-and-key (i.e., interdigitated) connection between the skull implant 102 and the soft tissue implant 104 is utilized at time of implantation. The interdigitated connection may be designed, for example as a "male-like" piece (i.e., catheter system) that penetrates into the soft side of a "female-shaped part" (i.e., fluid-filled chamber of neuromedicine like chemotherapy). The connection may have a tight fit so as to make sure there is no fluid extravasation and/or loss of electricity between the hard and soft tissue reconstruction components. The soft tissue component may be delivered in small-, medium-, or large-sized dimensions to accommodate different degrees of expected soft tissue resorption. An exemplary clinical scenario for such embodiments may be one where patients with pre-existing skull defects require neuroplastic surgery Second Embodiment As shown in FIG. 2, a second exemplary embodiment 200 offers the surgeon an "anatomy-specific soft tissue implant" for neurosurgical patients. In instances as neurotechnology becomes refined and with smaller footprints, it is conceivable that these functional devices could be pre-designed to fill-in soft tissue elements around the brain or spinal cord, instead of needing to replace both bone and soft tissue for placement. For example, a miniaturized implant one day could replace the temporalis muscle and temporal fat pad, have a medicine delivery chamber inside with MRI-lucent-pump-assisted technology, and then have miniaturized catheters connecting it through small skull holes into the brain. Accordingly, such embodiments may present a less invasive option for all patients in need of such, and furthermore by brain tumor patients that are in need of chronic infusion of brain tumor medicine and wishing to keep as much as their native skull as possible. For example, solid state batteries, RF charging advances, and rechargeable wireless batteries may make these devices much more miniaturized—and thus the smaller versions could be placed in areas filling only soft tissue above; for example, so as to only fill in the atrophic temporalis muscle and/or fat pad areas after repeat craniotomy consistent with post-neurosurgery temporal hollowing.

As such, a small-, medium-, and large-sized soft tissue implant component 204 may be delivered to the surgeon based on pre-operative CT scan assessment—which the surgeon may decide to use at time of cranioplasty based on intraoperative assessment and degree of soft tissue deformity identified at time of exploration—dependent on the type of central nervous system disease being treated and the size constraints provided by the implantable neurotechnology.

In the second exemplary embodiment 200, anatomy-specific craniofacial implants may be delivered as one implant following virtual fusion/shape creation by way of CT scanning and CAD/CAM design including: a) an anatomy-specific, soft tissue implant 204 with "high-profile" extension designed to replace missing temporalis muscle/fat/subcutaneous tissue, wherein the fabrication process provides a lock-and-key (i.e., interdigitated) connection for the soft tissue implant 204 to the healthy cranial bone 201 at time of implantation. The soft tissue component may be delivered in small-, medium-, or large-sized dimensions to accommodate different degrees of expected soft tissue resorption. An exemplary clinical scenario for such embodiments may be one where patients have pre-existing soft tissue defects following neurosurgical craniotomy defects requiring neuroplastic surgery.

Third Embodiment

Figure 3:
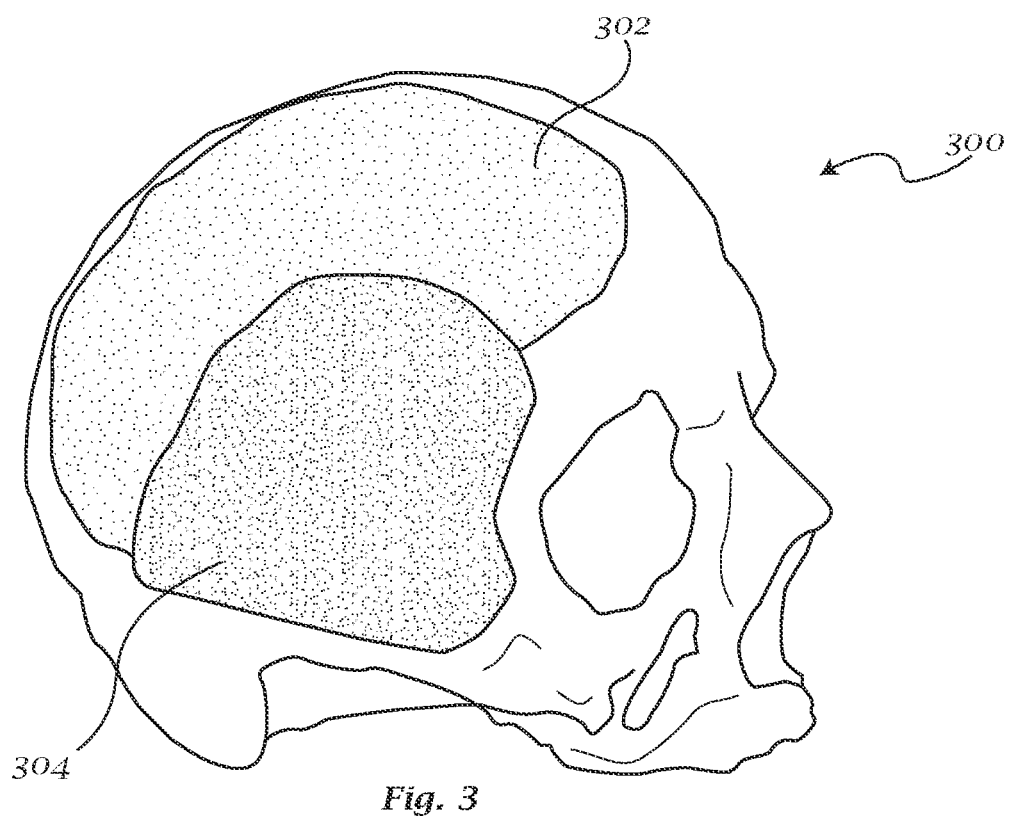
FIG. 3 shows a third exemplary embodiment of a multi-purpose implant, applicable to the cranium.

As shown in FIG. 3, a third exemplary embodiment 300 offers the surgeon an "anatomy-specific soft tissue implant" for neurosurgical patients in anticipation of future deformity. As such, a small-, medium-, and large-sized soft tissue implant component 304 may be delivered to the surgeon based on pre-operative CT scan assessment—which the surgeon may decide based on intraoperative assessment and degree of soft tissue mobilization identified at time of craniotomy.

In the third exemplary embodiment 300, anatomy-specific, multi-purpose craniofacial implants may be delivered as one implant following virtual fusion/shape creation by way of CT scanning and CAD/CAM design including: a) an anatomy-specific, soft tissue implant 304 designed to replace missing temporalis muscle/fat/subcutaneous tissue, wherein the fabrication process provides a lock-and-key (i.e., interdigitated) connection for the soft tissue implant 304 to the healthy cranial bone 301 at time of implantation. The soft tissue component may be delivered in small-, medium-, or large-sized dimensions to accommodate different degrees of expected soft tissue resorption. The soft tissue implant may be pre-embedded with life-changing or life-saving neurotechnologies (e.g., medicine delivery capabilities to bypass the blood-brain barrier) which may positively alter the function of the central nervous system and nearby brain, such as electronic neuromodulation, chemical modulation with medicine delivery, optical imaging for brain assessment, fluid diversion for hydrocephalic disease, therapeutic neuromodulation, enhanced brain performance, chronic neurological disease treatment of any kind, and/or improvement of memory storage. The soft tissue component may be delivered in small-, medium-, or large-sized dimensions to accommodate different degrees of expected soft tissue resorption. An exemplary clinical scenario for such embodiments may be one where patients have non-existing soft tissue defects but need planned neurosurgical craniotomy and neuroplastic surgery for instances like brain tumor resection.

Fourth Embodiment

Figure 4:
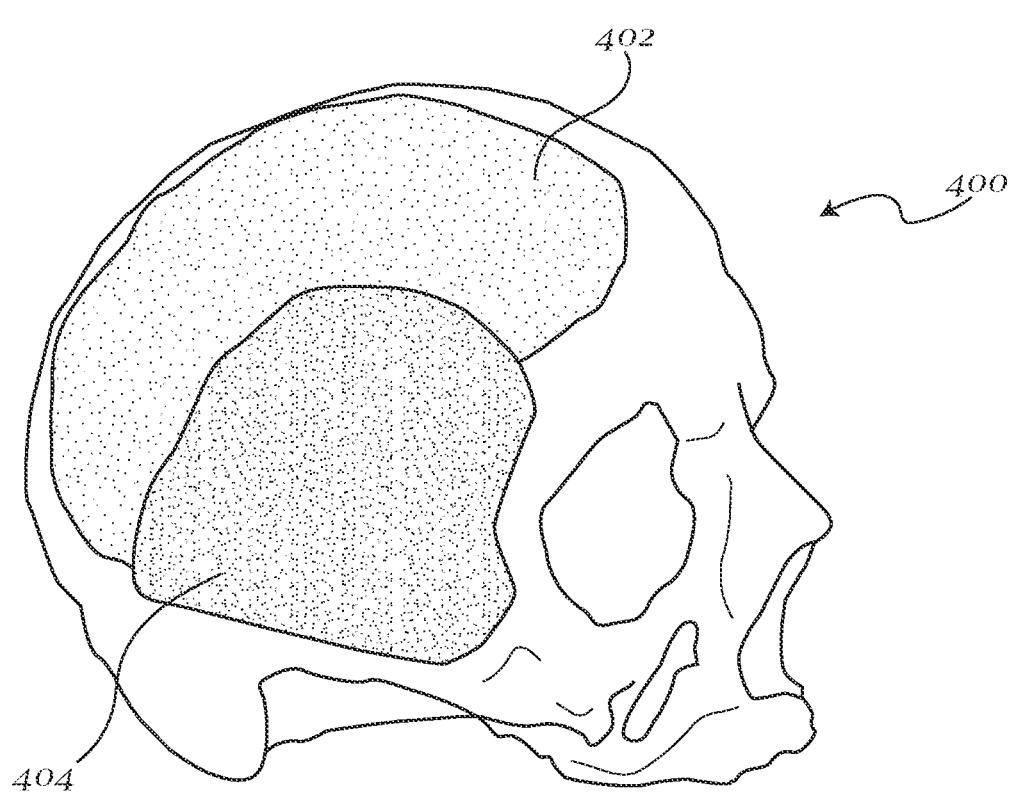
FIG. 4 shows a fourth exemplary embodiment of a multi-purpose implant, applicable to the cranium.

As shown in FIG. 4, in a fourth exemplary embodiment 400, another indication for use of the novel dual-purpose implants as described hereinabove, would be in instances of planned craniectomy (i.e., elective removal of non-diseased or normal cranial bone). Many neurosurgical procedures are planned on brain disease for which is covered by normal, healthy bone (for patients who have never had surgery in the targeted area and have undisrupted anatomy present). However, as the field of neurotechnology continues to expand, the use of implantable neurotechnology will require elective removal of bone and soft tissue to make room for these space-occupying devices for which can be life-changing or life-saving. For example, current day and futuristic devices can deliver medicine for chronic neurological disease like cancer, epilepsy, neurodegenerative disease, post-traumatic stress disorders (PTSD), attention-deficit hyperactivity disease (ADHD), movement tremor disease, memory deterioration, poor performance related to age, brain enhancement, stress-related environments, etc. In addition, these neurotech devices could house imaging devices to avoid necessary CT scans or MRIs post-operatively. Such devices may also house hydrocephalic shunting mechanisms and/or photoelectric neuromodulatory components, with or without wireless charging platforms based on RF technology. Regardless of inherent function, such devices require space to avoid impingement on the underlying brain and subtle scalp above. Thus, this novel "dual-purpose implant" would have the anatomy-specific design to fit into each patient's exact dimensions for both the bone and soft tissue being electively removed. Thus, the two-piece design—one being the skull implant 402 and the other being the soft tissue implant 404 would be fitted together intraoperatively based on small, medium, or large-size expected soft tissue resorption assessed by the surgeon. Hence, such embodiments offer the surgeon a two-piece design with a standard cranial bone replacement implant 402, along with a small-, medium-, and large-sized soft tissue implant component 404—for which the surgeon can decide to use at time of craniectomy based on intraoperative assessment and degree of soft tissue resorption.

In the fourth exemplary embodiment 400, anatomy-specific craniofacial implants can be delivered as two separate implants following virtual fusion/shape creation by way of CT scanning and CAD/CAM design including: a) a skull implant 402 designed to reconstruct/replace a defect for a planned craniectomy (i.e., elective removal of cranial bone; or non-existing skull defect); and b) a soft tissue implant 404 designed to prophylactically restore (i.e., some degree of atrophy is expected by the surgeon) temporalis muscle/fat, wherein the fabrication process provides two implants to the surgeon and a lock-and-key (i.e., interdigitated) connection between the skull implant 402 and the soft tissue implant 404 is utilized at time of implantation. The soft tissue component could be delivered in small-, medium-, or large-sized dimensions to accommodate different degrees of expected soft tissue resorption. An exemplary clinical scenario for such embodiments may be one where patients with non-existing skull defects require planned craniectomy and neuroplastic surgery.

Fifth and Sixth Embodiments

The brain is a complex organ which has no current substitute, as opposed to the human heart, lung, liver or kidney, as disclosed in Gordon, "The Special Field of Neuroplastic Surgery" published in the *Journal of Craniofacial Surgery* [2021 Jan.-Feb. 1; 32(1):3-7. (www.hopkinsmedicine.org/Neuroplastic-Surgery/about.html), the disclosure of which is incorporated herein in its entirety. Thus, the only way to manipulate the diseased or aging brain is to place a wireless powered device which has the ability to alter brain function by way of medicine, electricity, neuroimaging, non-invasive neuromodulation, and/or photooptics. Such devices have size constraints due to challenging craniofacial anatomy and require strategic placement within a biocompatible compartment. However, there is not much extra space within the human head and within the cranial space. Strategically, the skull bone space is the ideal placement position—as disclosed in U.S. Pat. No. 11,058,541, "Low-profile Intercranial Device" (i.e., "intercranial" referring to the space within the cranial bone). Thus, for patients who have pre-existing skull defects and are in need of planed cranioplasty reconstruction by way of neuroplastic surgery, the embodiments disclosed herein may provide an improved treatment strategy. However, for the purpose of brain medicine delivery via temporal implants—based on pump-assisted, multiphase flow circuits, wireless charging platforms, embedded biosensors, and many other functional components—the skull space becomes heavily crowded and shown to be a non-viable option to the present inventor. First, a dual-purpose implant may have a skull implant designed to replace missing cranioplasty bone (i.e., pre-existing defects), and, secondly, a soft tissue part may be provided, which has an embedded functional component having, for example, neurotechnologies for life-changing, life-saving, and brain-altering capabilities. Of particular note, the cranial bone space of about 4-12 millimeters may not provide sufficient space for current medicine-delivery designs, especially as the technological applications further develop; thus, the embodiments disclosed herein are adapted to house embedded neurotechnologies within the overlying soft tissue part, as an anatomy-specific design (with a new thickness of about 13-40 mm by way of adding soft tissue, "extracranial" space). Additionally, this extra extension up towards the skin (i.e., high-profile extension) may allow better transcutaneous needle access, as in the case of chronic medicine delivery and refillable reservoirs, and may allow for less soft tissue interference when related to Bluetooth module/wireless RF charging connectivity. Also, as a patient ages and their neurological disease changes with respect to time, such a soft tissue part may be interchanged in "plug-and-play" fashion, by decoupling the such from the cranial implant and installing a new soft tissue part. Within the soft tissue aspect of this implant, a functional component may be embedded, and the functional component may include life-changing/life-saving neurotechnologies as well as provide swappable medicine chambers; such technologies and medicines may positively alter the function of the central nervous system and nearby brain, such as: electronic neuromodulation, chemical modulation with medicine delivery, optical imaging for brain assessment, fluid diversion for hydrocephalic disease, hands-free connectivity to wireless communication devices, prevention of chronic symptoms, reversal of age deterioration, remote imaging devices for real-time, remote assessment, and/or improvement of memory storage and function. A similar design is applicable for spinal reconstruction as well, as disclosed in Gordon, et al., "First-in-human Experience with Integration of a Hydrocephalus Shunt Device Within a Customized Cranial Implant"; Featured Cover Image, Operative Neurosurgery; December 2019 Issue, the disclosure of which is incorporated herein in its entirety.

Figure 5:
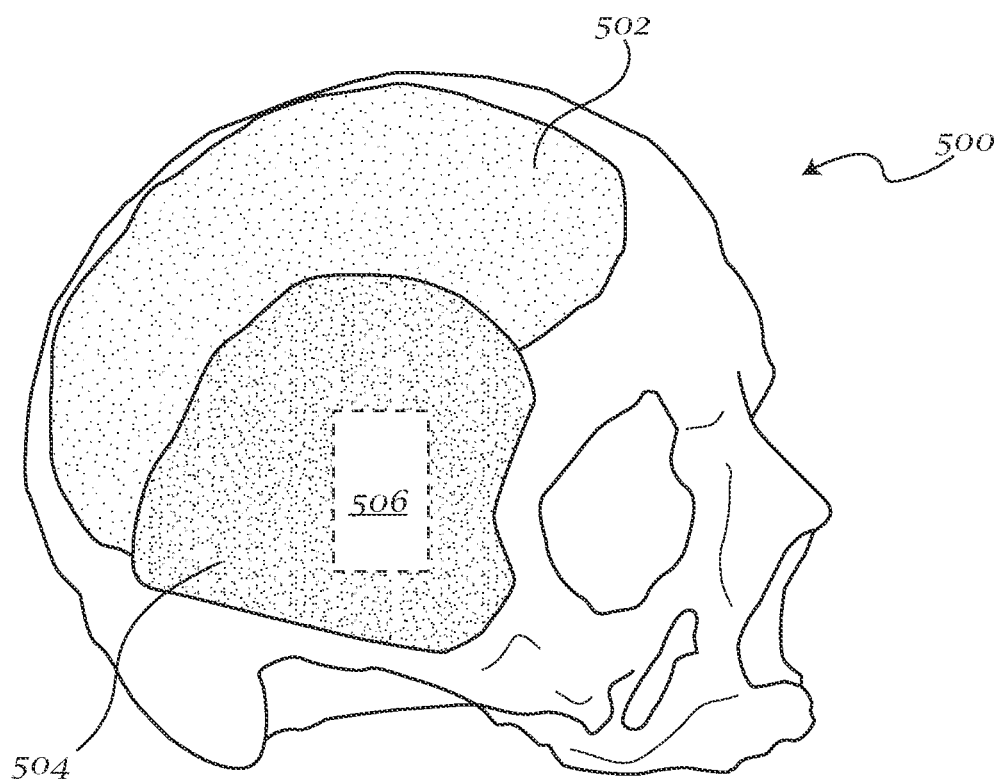
FIG. 5 shows a fifth exemplary embodiment of a multi-purpose implant, applicable to the cranium.

As shown in FIG. 5, in a fifth exemplary embodiment 500, anatomy-specific craniofacial implants may be delivered as two separate implants following virtual fusion/shape creation by way of CT scanning and CAD/CAM design including: a) a skull implant 502 designed to replace missing cranial bone (i.e., pre-existing skull defect); and b) a soft tissue implant 504 designed to replace missing temporalis muscle/fat/subcutaneous tissue, wherein the fabrication process provides two implants to the surgeon and a lock-and-key (i.e., interdigitated) connection between the skull implant 502 and the soft tissue implant 504 is utilized at time of implantation; and wherein the soft tissue implant 504 is embedded with a functional component 506 having, for example, life-changing or life-saving neurotechnologies which positively alter the function of the central nervous system and nearby brain such as electronic neuromodulation, chemical modulation with medicine delivery, optical imaging for brain assessment, fluid diversion for hydrocephalic disease, therapeutic neuromodulation, chronic symptom reversal, function enhancement, prevention of age-related deterioration, and/or improve memory storage. The soft tissue component 504 could be delivered in small-, medium-, or large-sized dimensions to accommodate different degrees of expected soft tissue resorption. An exemplary clinical scenario for such embodiments may be one where patients with pre-existing skull defects require neuroplastic surgery and placement of an embedded functional component 506 strategically housed within soft tissue component 504 to address an underlying neurological disease.

Figure 6:
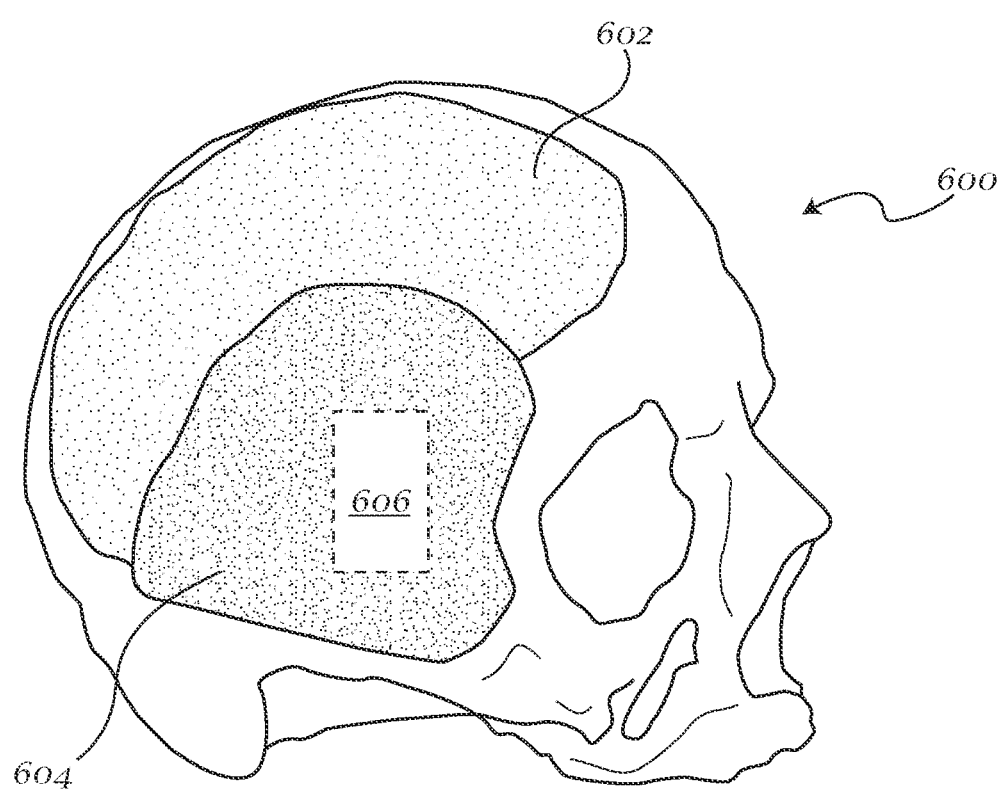
FIG. 6 shows a sixth exemplary embodiment of a multi-purpose implant, applicable to the cranium.

As shown in FIG. 6, in a sixth exemplary embodiment 600, anatomy-specific craniofacial implants can be delivered as two separate implants following virtual fusion/shape creation by way of anatomical averaging for standard sizes and/or CT scanning with CAD/CAM, patient-specific design including: a) a skull implant 602 designed to replace bone following planned craniectomy (i.e., non-existing skull defect); and b) a soft tissue implant 604 designed to replace missing temporalis muscle/fat/subcutaneous tissue, wherein the fabrication process provides two implants to the surgeon and a lock-and-key (i.e., interdigitated) connection between the skull implant 602 and the soft tissue implant 604 is utilized at time of implantation; and wherein the soft tissue implant 604 is embedded with a functional component 606 having, for example, life-changing or life-saving neurotechnologies which may positively alter the function of the central nervous system and nearby brain, such as: electronic neuromodulation, chemical modulation with medicine delivery, optical imaging for brain assessment, fluid diversion for hydrocephalic disease, therapeutic neuromodulation, and/or improvement of memory storage. The soft tissue component 604 may be delivered in small-, medium-, or large-sized dimensions to accommodate different degrees of expected soft tissue resorption. An exemplary clinical scenario for such embodiments may be one where patients with non-existing skull defects in need of planned craniectomy and neuroplastic surgery require brain surgery and require placement of an embedded functional component 606 housed within soft tissue implant 604 to address an underlying neurological disease.

Spinal Embodiments

Seventh and Eighth Embodiments

The act of spine surgery for cancer and/or trauma often requires some form of planned bone removal or decompression to make space for access to the spinal cord. Most recently, novel technologies are being designed to alter impaired spinal cord function such as paralysis reversal, tremor, chronic pain, acute trauma, and/or weakness. Thus, the paraspinal anatomy (i.e., overlying muscle/fat) may inevitably become distorted at time of planned surgery due to devascularization and deinnervation of critical structures such as the paraspinal musculature. As such, contour irregularities on the back and visual deformities may be forever jeopardized following the breach of this critical anatomy. Unfortunately, the art and science of manmade alloplastic implants for craniofacial and spinal reconstruction arose in the 1990's but solely concentrated on replacing the missing bone with patient-specific design. The present inventor had previously invented the first description of patient-specific craniofacial implants to replace the missing soft tissue at the same time of skull reconstruction, by employing novel computer-assisted design algorithms. The present inventor had invented an improved design for which involves better-defined anatomical vector lines for improved consistency (i.e., enhanced results), a pre-fabricated temporal window to prevent soft tissue impingement at time of placement, and the first-ever description of placing these craniofacial implants above the scarred-down temporalis muscle as opposed to underneath it. This was first described by the present inventor in his sentinel article entitled "Temporal augmentation with methyl methacrylate" in September 2011, as a way to use hand-shaped, alloplastic implants for simultaneous soft tissue and/or hard tissue deformity correction using a primitive approach and hand-eye modification. (Gordon, et al. *Aesthetic Surgery Journal;* 31(7):827-33.) However, the surgeon is also limited in these inventions by the fact that these "dual-purpose craniofacial implants" (wherein the first purpose is replacing missing bone for brain protection and the second purpose is restoring facial symmetry secondary to soft tissue deformity) are delivered as one larger implant, as disclosed in Zhong et. al., "Quantitative Analysis of Dual-Purpose, Patient-Specific Craniofacial Implants for Correction of Corporal Deformity", the disclosure of which is incorporated herein in its entirety. Hence, the embodiments disclosed herein offer the spine surgeon a two-piece design with a standard vertebral bone replacement implant, such as a laminoplasty for example, along with a small-, medium-, and large-sized soft tissue implant component—which the surgeon can decide to use at time of spine surgery based on intraoperative assessment and degree of soft tissue resorption.

Figure 7:
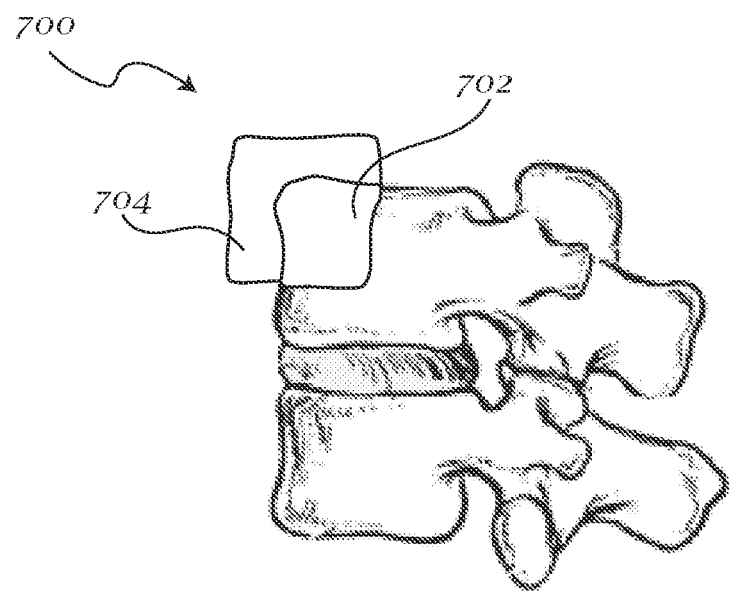
FIG. 7 shows a seventh exemplary embodiment of a multi-purpose implant, applicable to the spine.

As shown in FIG. 7, in a seventh exemplary embodiment 700, anatomy-specific spinal implants may be delivered as two separate implants following virtual fusion/shape creation by way of CT scanning and CAD/CAM design including: a) a spinal bone implant 702 designed to replace missing vertebral bone (i.e., pre-existing spinal defect following previous spinal cord decompression surgery such as laminectomy/laminoplasty and/or traumatic injury); and b) a soft tissue implant 704 designed to replace missing paraspinal muscle/fat wherein the fabrication process provides two implants to the surgeon and a lock-and-key (i.e., interdigitated) connection between the spinal bone implant 702 and the soft tissue implant 704 is utilized at time of implantation. The soft tissue component 704 may be delivered in small-, medium-, or large-sized dimensions to accommodate different degrees of expected soft tissue resorption. An exemplary clinical scenario for such embodiments may be one where patients with pre-existing, post-operative spinal column defects require neuroplastic surgery.

Figure 8:
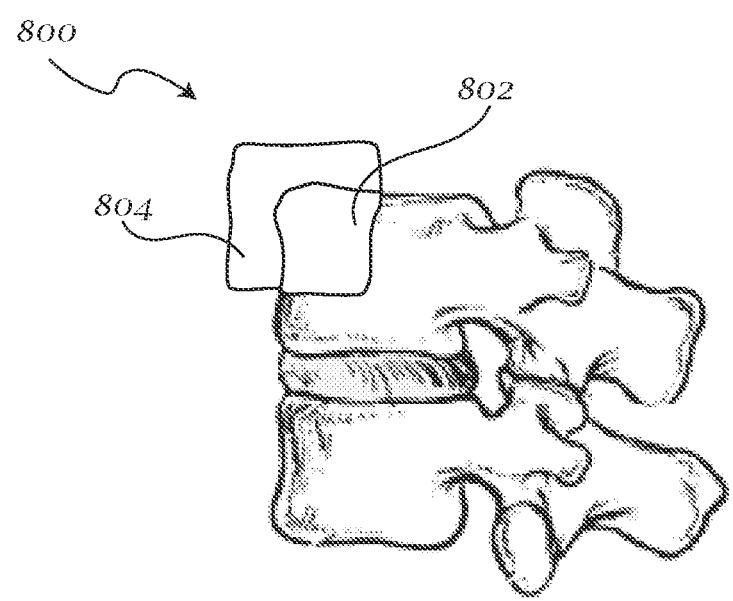
FIG. 8 shows an eighth exemplary embodiment of a multi-purpose implant, applicable to the spine.

As shown in FIG. 8, in an eighth exemplary embodiment, anatomy-specific spinal implants may be delivered as two separate implants following virtual fusion/shape creation by way of CT scanning and CAD/CAM design including: a) a spinal bone implant 802 designed to replace planned resection of vertebral bone (i.e., non-existing bone defect; planned spinal cord decompression such as laminectomy/laminoplasty and/or traumatic injury); and b) a soft tissue implant 804 designed to replace missing paraspinal muscle/fat wherein the fabrication process provides two implants to the surgeon and a lock-and-key (i.e., interdigitated) connection between the spinal bone implant 802 and the soft tissue implant 804 is utilized at time of implantation. The soft tissue component 804 may be delivered in small-, medium-, or large-sized dimensions to accommodate different degrees of expected soft tissue resorption. An exemplary clinical scenario for such embodiments may be one where patients with non-existing defects require planned bone removal, placement of embedded neurotechnology, and neuroplastic surgery.

Further Spinal Embodiments

The spinal cord, as a component of the central nervous system, is a complex organ for which has no current substitute, as opposed to the human heart, lung, liver or kidney, as disclosed in Gordon, "The Special Field of Neuroplastic Surgery" published in the *Journal of Craniofacial Surgery* [2021 Jan.-Feb. 1; 32(1):3-7, (www.hopkinsmedicine.org/Neuroplastic-Surgery/about.html), the disclosure of which is incorporated herein in its entirety. Thus, the only way to manipulate a diseased, traumatized and/or aging spinal cord is to place a device which has the ability to alter spinal cord function by way of medicine, electricity, real-time, remote neuroimaging with wireless connectivity, non-invasive neuromodulation, and/or photooptics. Such devices have size constraints and require strategic placement within a biocompatible compartment. However, there is not much extra space within the human spine and back. Strategically, the bone space above the brain and spinal cord is therefore the ideal placement position—as disclosed in U.S. Pat. No. 11,058,541, "Low-profile Intercranial Device"—but the present inventor has realized that medicine delivery technology needs more than just "bone-only" volume. However, as the temporal multipurpose devices become more miniaturized over several iterations, the soft tissue space may allow for placement of a two-piece design implant, thereby removing the severity of surgery when "plug-and-play" switching is needed, and minimizing the need for bone removal altogether.

Ninth and Tenth Embodiments

Thus, for patients who have pre-existing spine defects from previous surgeries and are in need of planned reconstruction by way of neuroplastic surgery, such embodiments may provide an improved treatment strategy. First, a dual-purpose implant may have a spinal implant designed to replace missing vertebral bone (i.e., pre-existing defects), and, second, a soft tissue implant may be provided which may include a functional component having embedded neurotechnologies for life-changing/life-saving, spinal cord-altering capabilities. Of particular note, the vertebral bone space is just a few millimeters and is often not enough space for current designs; thus, the embodiments disclosed herein can house embedded neurotechnologies within the soft tissue implant space. Furthermore, as one ages and their neurological disease changes with respect to time, the soft tissue implant may be interchanged in a "plug-and-play" fashion, for example by decoupling it from the spinal implant and using a new soft tissue implant. Within the soft tissue aspect of the implant, a functional component having, for example, life-changing/life-saving neurotechnologies may be embedded, which may positively alter the function of the central nervous system and nearby spinal cord, such as: electronic neuromodulation, chemical modulation with medicine delivery, real-time, remote optical imaging for blood flow assessment with wireless connectivity, fluid diversion for trauma or disease, improvement of paralysis, fluid diversion for hydrocephalic disease, hands-free connectivity to wireless communication devices for patient provider interpretation, reversal of paralysis, and/or improvement of strength/balance. Of note, in instances of implantable neurotechnology devices becoming more refined with smaller footprints over time, it is conceivable that these functional devices could be pre-designed to fill-in soft tissue elements around the brain or spinal cord, instead of needing to replace both bone and soft tissue for placement. For example, solid state batteries and rechargeable wireless platforms with radio signals (i.e., RF technology) may make these devices more miniaturized—and thus the smaller versions could be placed in areas filling only soft tissue above. This would mean that switching the outer piece for a different, disease-specific technology may be less invasive since the bone space would not be invaded during repeat surgery.

Figure 9:
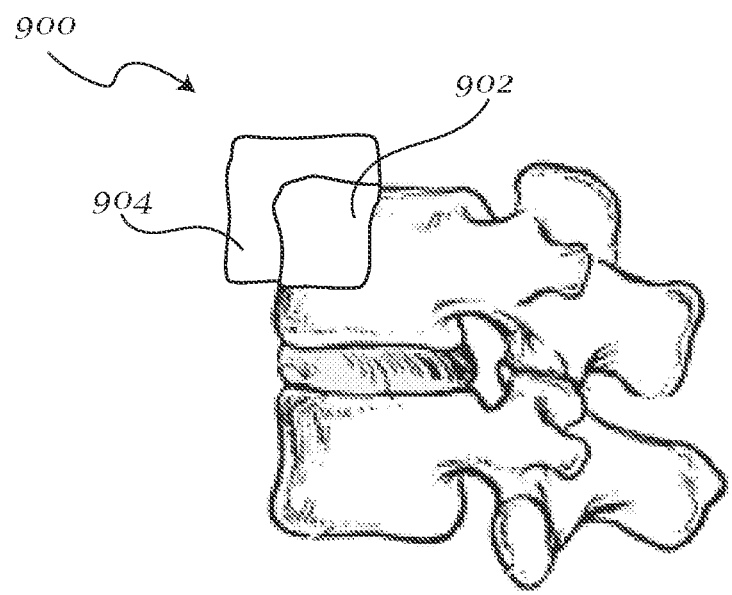
FIG. 9 shows a ninth exemplary embodiment of a multi-purpose implant, applicable to the spine.

As shown in FIG. 9, In a ninth exemplary embodiment 900, anatomy-specific spinal implants may be delivered as two separate implants following virtual fusion/shape creation by way of CT scanning and CAD/CAM design including: a) a spinal bone implant 902 designed to replace vertebral bone following planned decompression (i.e. non-existing spine defect); and b) a soft tissue implant 904 designed to replace missing paraspinal muscle/fat/subcutaneous tissue, wherein the fabrication process provides two implants to the surgeon and a lock-and-key (i.e., interdigitated) connection between the spinal bone implant 902 and the soft tissue implant 904 is utilized at time of implantation; and wherein the soft tissue implant 904 includes a functional component 906, which may, for example, include life-changing or life-saving neurotechnologies which positively alter the function of the central nervous system and nearby spinal cord such as electronic neuromodulation, chemical modulation with medicine delivery, optical imaging for brain assessment, fluid diversion for hydrocephalic disease, therapeutic neuromodulation, prevention of age deterioration, performance enhancement for sports, and/or improvement of memory storage. The soft tissue component 904 may be delivered in small-, medium-, or large-sized dimensions so as to accommodate different degrees of expected soft tissue resorption. An exemplary clinical scenario for such embodiments may be one where patients with pre-existing spinal column defects require neuroplastic surgery and placement of an embedded neurotechnology device 906 strategically housed within the soft tissue implant 904 to address an underlying spinal cord disease. Not having to go into the bone space greatly lessens the invasiveness of future surgeries as the outer component gets switched out—for instances like medicine chamber refills, battery exchange, hardware updates, or change is neurological disease and updating corresponding applications of relevance.

Figure 10:
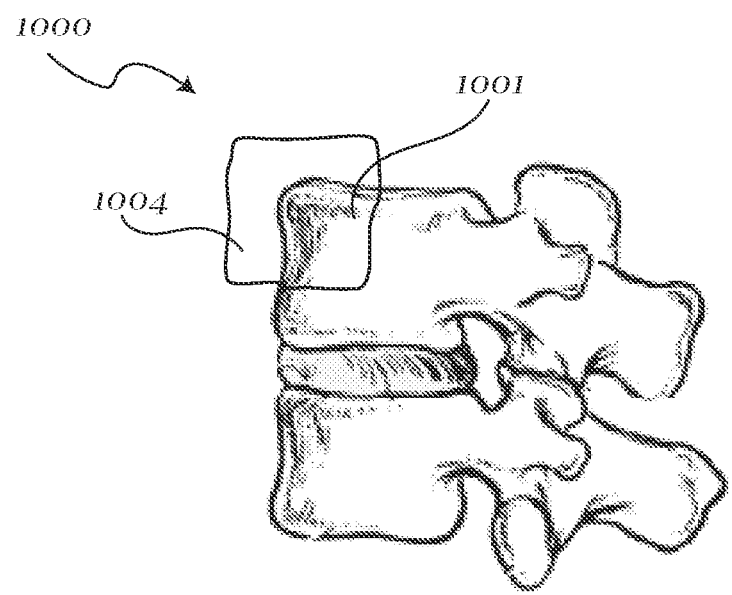
FIG. 10 shows a tenth exemplary embodiment of a multi-purpose implant, applicable to the spine.

As shown in FIG. 10, in a tenth exemplary embodiment 1000, anatomy-specific spinal implants may be delivered as one implant following virtual fusion/shape creation by way of CT scanning and CAD/CAM design, including: a) an anatomy-specific, soft tissue implant 1004 designed to replace missing paraspinal muscle/fat, wherein the fabrication process provides a lock-and-key (i.e., interdigitated) connection for the soft tissue implant 1004 to the healthy vertebral bone 1001 at time of implantation. The soft tissue component 1004 may be delivered in small-, medium-, or large-sized dimensions so as to accommodate different degrees of expected soft tissue resorption. An exemplary clinical scenario for such embodiments may be one where patients with pre-existing soft tissue defects following previous spine surgery require neuroplastic surgery and placement of an embedded neurotechnology device strategically housed within soft tissue implant 1004 to address an underlying spinal cord disease.

Eleventh Embodiment

Figure 11:
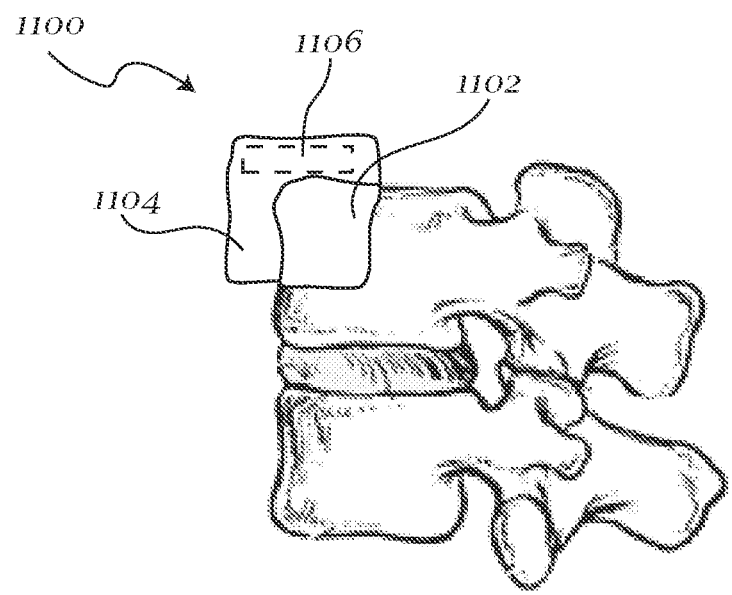
FIG. 11 shows an eleventh exemplary embodiment of a multi-purpose implant, applicable to the spine.

As shown in FIG. 11, in an eleventh exemplary embodiment 1100, for patients who require some form of planned decompression and/or implanted neurotech device, such embodiments may provide improved treatment strategy. First, a dual-purpose implant 1100 may have a bone implant 1102 designed to replace missing vertebral bone (i.e., pre-existing defects), and, second, a soft tissue implant 1104 may be provided which may include an embedded functional component 1106 having, for example, neurotechnologies for life-changing/life-saving, spinal cord-altering capabilities. Of particular note, the vertebral bone space is just a few millimeters and is often not enough space for current designs; thus, the embodiments disclosed herein can house embedded neurotechnologies within the soft tissue implant space. Furthermore, as one ages and their neurological disease changes with respect to time, the soft tissue implant 1104 may be interchanged in a "plug-and-play" fashion, for example by decoupling it from spinal bone implant 1102 and using a new soft tissue implant 1104. Within the soft tissue aspect of the implant 1104, a functional component 1106 may be embedded, which may positively alter the function of the central nervous system and nearby spinal cord, such as: electronic neuromodulation, chemical modulation with medicine delivery, optical imaging for blood flow assessment, fluid diversion for trauma, prevention of age-related deterioration, performance enhancement, resolution of chronic disease, reversal of lower/upper extremity paralysis, fluid diversion for hydrocephalic disease, hands-free connectivity to wireless communication devices, reversal of paralysis, and/or improvement of strength/balance.

In the eleventh exemplary embodiment 1100, anatomy-specific spinal implants may be delivered as two separate implants following virtual fusion/shape creation by way of CT scanning and CAD/CAM design including: a) a spinal bone implant 1102 designed to replace vertebral bone following planned decompression (i.e., non-existing spine defect); and b) a soft tissue implant 1104 designed to replace missing paraspinal muscle/fat/subcutaneous tissue, wherein the fabrication process provides two implants to the surgeon and a lock-and-key (i.e., interdigitated) connection between the spinal bone implant 1102 and the soft tissue implant 1104 is utilized at time of implantation; and wherein the soft tissue implant 1104 is embedded with a functional component 1106 having, for example, life-changing or life-saving neurotechnologies which positively alter the function of the central nervous system and nearby spinal cord such as electronic neuromodulation, chemical modulation with medicine delivery, optical imaging for brain assessment, fluid diversion for hydrocephalic disease, therapeutic neuromodulation, prosthetic limb control, and/or improvement of memory storage. The soft tissue component 1104 may be delivered in small-, medium-, or large-sized dimensions so as to accommodate different degrees of expected soft tissue resorption. An exemplary clinical scenario for such embodiments may be one where patients with non-existing spinal column defects (i.e., planned surgery) require neuroplastic surgery and placement of an embedded functional component 1106 strategically housed within soft tissue implant 1104 to address an underlying spinal cord disease.

Twelfth Embodiment

Figure 12:
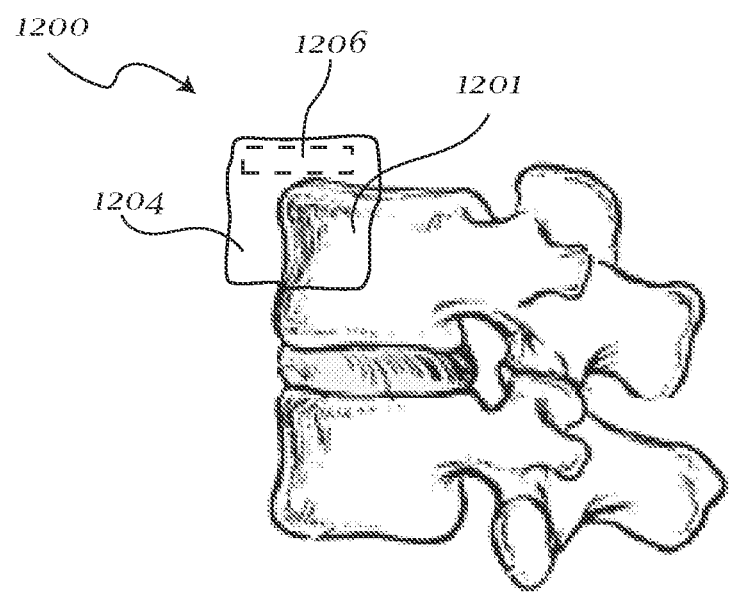
FIG. 12 shows a twelfth exemplary embodiment of a multi-purpose implant, applicable to the spine.

As shown in FIG. 12, in a twelfth exemplary embodiment 1200, for patients in need of planned spinal cord surgery and reconstruction by way of neuroplastic surgery, such embodiments may provide an improved treatment strategy via neuroplastic surgery. As implantable neurotechnology devices becoming more refined with smaller footprints—for the purpose of embedding within "anatomy-specific implant" encasements, it is conceivable that these functional devices could be pre-designed to fill-in soft tissue elements around the spinal cord, instead of needing to replace both bone and soft tissue for placement. For example, pump-assisted delivery systems with medicine, solid state batteries and rechargeable wireless platforms (i.e., RF technology) with radio signals may make these devices much more miniaturized—and thus the smaller versions could be placed in areas filling only soft tissue above the spine, like within the paraspinal musculature. This would mean that switching the outer piece for a different, disease-specific technology may be less invasive since the bone space would not be invaded during repeat surgery. Furthermore, as one ages and their neurological disease changes with respect to time, the soft tissue implant 1204 may be interchanged in a "plug-and-play" fashion, for example by decoupling it from healthy vertebral bone 1201 and using a new soft tissue implant 1204. Within the soft tissue aspect of the implant 1204, a functional component 1206 having, for example, life-changing/life-saving neurotechnologies may be embedded, which may positively alter the function of the central nervous system and nearby spinal cord, such as: electronic neuromodulation, chemical modulation with medicine delivery, optical imaging for blood flow assessment, fluid diversion for trauma or disease, improvement of paralysis, fluid diversion for hydrocephalic disease, hands-free connectivity to wireless communication devices, reversal of paralysis, and/or improvement of strength/balance.

In the twelfth embodiment 1200, anatomy-specific spinal implants may be delivered as one implant following virtual fusion/shape creation by way of CT scanning and CAD/CAM design, including: a) an anatomy-specific, soft tissue implant 1202 designed to replace missing paraspinal muscle/fat/subcutaneous tissue, wherein the fabrication process provides a lock-and-key (i.e., interdigitated) connection for the soft tissue implant 1202 to the healthy vertebral bone 1201 at time of implantation. The soft tissue component 1202 may be delivered in small-, medium-, or large-sized dimensions to accommodate different degrees of expected soft tissue resorption. This soft tissue implant 1202 may be embedded with a functional component 1206 having, for example, life-changing or life-saving neurotechnologies which may positively alter the function of the central nervous system and nearby spinal cord such as electronic neuromodulation, chemical modulation with medicine delivery, optical imaging for brain assessment, fluid diversion for hydrocephalic disease, therapeutic neuromodulation, and/or improvement of memory storage. The soft tissue functional component 1206 may be delivered in small-, medium-, or large-sized dimensions to accommodate different degrees of expected soft tissue resorption. An exemplary clinical scenario for such embodiments may be one where patients with non-existing soft tissue defects in need of planned spine surgery require neuroplastic surgery and placement of an embedded neurotechnology device strategically housed within the soft tissue implant 1204 so as to address an underlying spinal cord disease.

Figure 14:
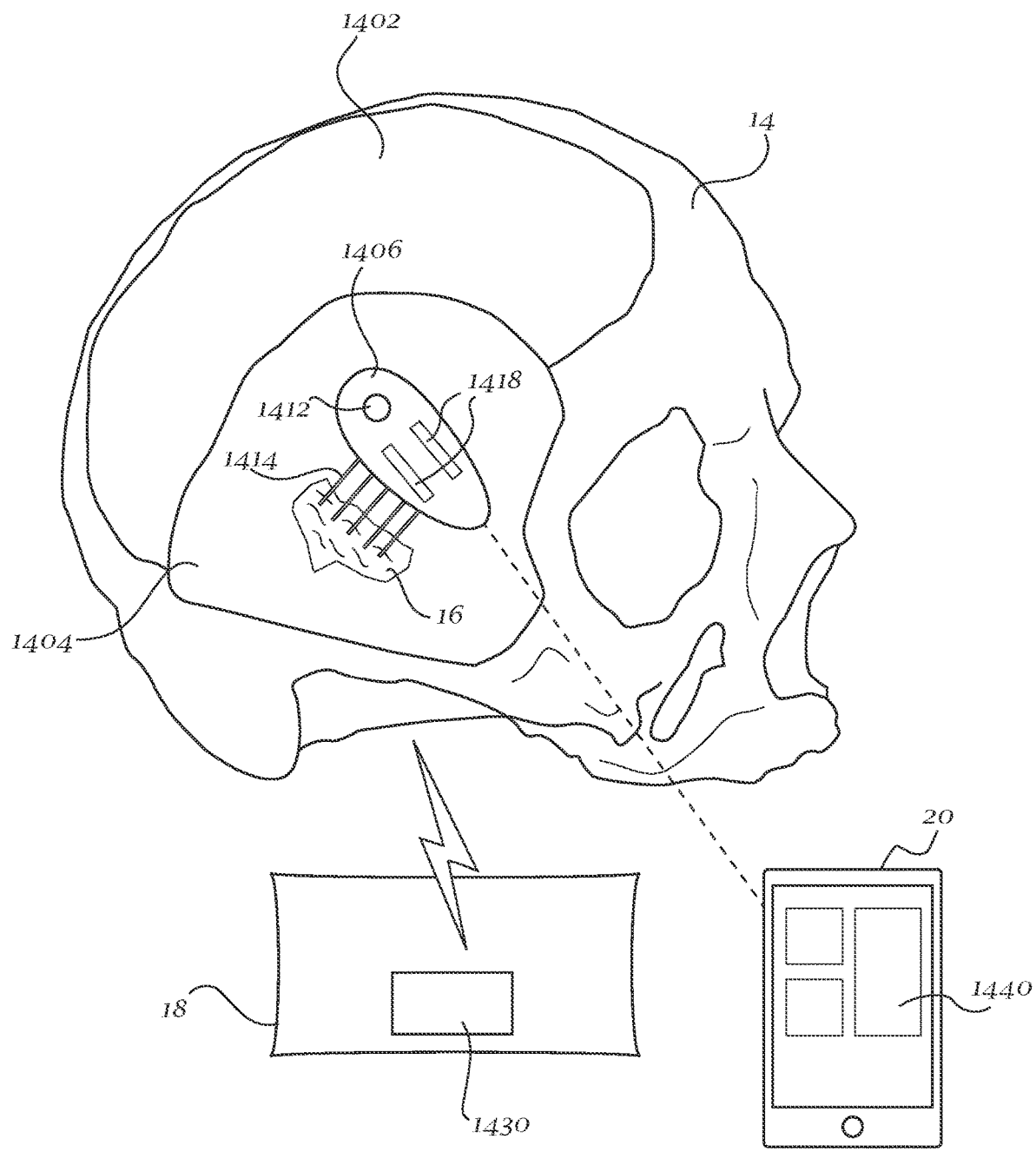
FIG. 14 shows a fourteenth exemplary embodiment of a multi-purpose implant, applicable to the cranium.

It should be appreciated that the embodiments disclosed herein may further be modified without departing from the spirit of the invention. In some embodiments, rather than a lock-and-key fit, the bone implant and soft tissue implant may be fused during the fabrication process or "click-in" using a plug or adapter, designed for intra-operative manipulation, or may include a switch for post-operative manipulation. The embedded neurotechnologies may further include, but are not limited to, any technology capable of or adapted to brain or spine modulation, for example to deliver medicine, control disease, remove or cure dysfunction, restore traumatized brain or spinal cord, or to improve or superficially augment the aging central nervous system with external, wireless connections. Some such neurotechnologies are shown in FIG. 14. Furthermore, in some embodiments, soft-tissue-only dual-purpose implants may include a small catheter, filament or wire passed through the bone into the brain or spinal cord, so as to allow wireless connectivity to the external world and/or to deliver pump-assisted, connection-enhanced delivery for bypassing the blood-brain barrier.

Furthermore, in some embodiments, the implants may be constructed of any materials that enable them to function as described herein, for example various man-made biomaterials and/or 3D printed tissue. The biomaterials may furthermore be radiolucent, for unimpeded wireless connectivity such as Bluetooth, sonolucent, for unimpeded sonography (both diagnostic and therapeutic), and visually clear, for improved surgery placement accuracy including bleeding inspection and reducing the likelihood of impingement on the brain or spinal cord underneath during fixation with hardware. More than one spinal or cranial implant may be used, for example, coupled to several vertebrae or a as bilateral cranial implant.

Functional Component Embodiment

Figure 13:
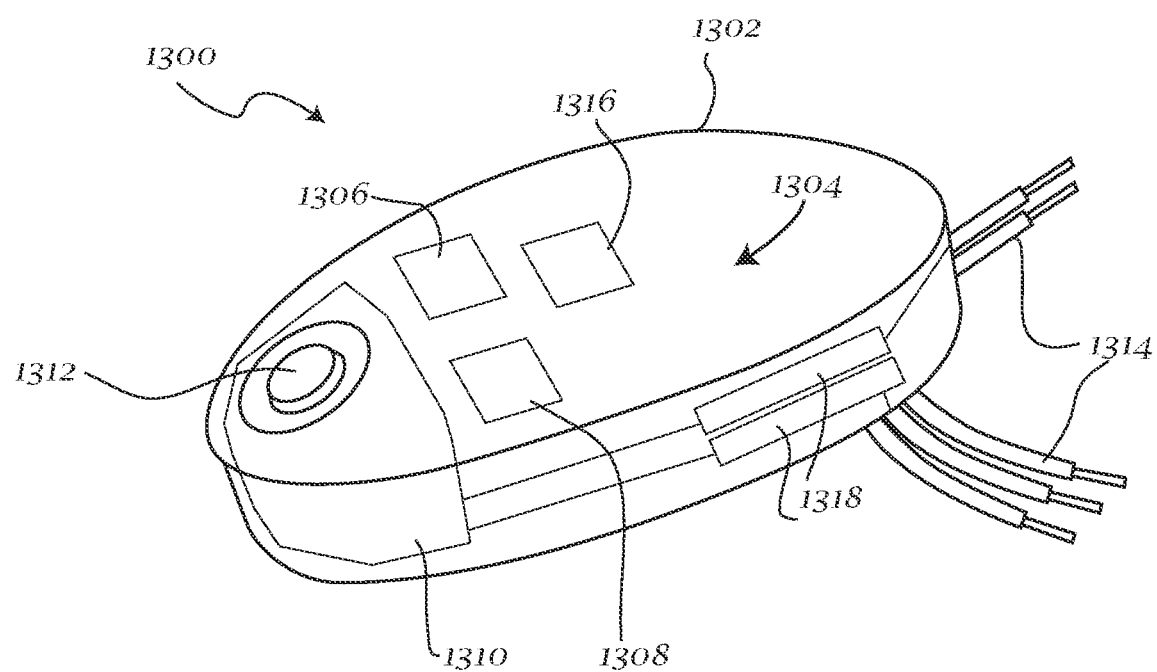
FIG. 13 shows a thirteenth exemplary embodiment of a multi-purpose implant, applicable to the cranium.

FIG. 13 shows an exemplary functional component 1300 which may be used with the embodiments of the implants described hereinabove. The functional component can be sized and shaped to fit within the temporal fossa, and further within embodiments of the soft tissue implant described herein. The functional component 1300 may include a housing 1302, one or more electronic components 1304, which may include a central processing unit 1306 and a rechargeable battery 1308. The functional component 1300 may further include a refillable reservoir 1310 having a cover or diaphragm 1312 that may be penetrable by a percutaneous or similar needle. The functional component 1300 may further include a plurality of conduits or catheters 1314, for example five catheters that may have length such that they can penetrate subdurally approximately 2-5 centimeters deep into the brain. Additional electronic components disposed within functional component 1300 may include, but are not limited to, a Bluetooth module 1316, at least one electro-osmotic pump 1318, Furthermore, rechargeable battery 1308 may utilize wireless charging so as to be able to charge from a distance, for example up to 18 inches away from functional component 1300 (i.e., the charging portion may be placed under a pillow or within the pillowcase of the patient needing device-charging overnight, or within a headwear having internal components to allow charging during the daytime).

Furthermore, the cover or diaphragm 1312 may protrude above the surrounding surface of housing 1302, such that the diaphragm and "high-profile" design may be easily palpable under the skin to improve safety and efficacy of needle filling. It should be appreciated that this is in contrast to a "low-profile" intercranial design, wherein the functional component would have a smooth contour with normal bone all around, and therefore not be palpable by one's fingers rubbing along the skin's surface, and presenting an impediment to percutaneous refilling of a reservoir. The present functional component 1300, however, extends within the soft tissue implant, and therefore allows, for example, digital palpating prior to refilling with a percutaneous needle by having a palpable ring structure surrounding the self-sealing diaphragm.

Furthermore, the cover or Bluetooth module/wireless RF charging platform 1316 may protrude above the surrounding surface of housing 1302, such that the diaphragm and "high-profile" design may be easily palpable under the skin to improve safety and efficacy of wireless connectivity. It should be appreciated that this is in contrast to a "low-profile" intercranial design, wherein the functional component would have a smooth contour with normal bone all around, and would have a fully thick scalp and soft tissue element covering it, and therefore presenting an impediment to wireless charging and/or Bluetooth connectivity. The present functional component 1300, however, extends within the soft tissue implant, and therefore allows, for example, more effective and safer wireless communication and/or charging.

According to the embodiments disclosed herein, FIG. 14 shows a hard tissue implant 1402 and soft tissue implant 1404, coupled to a skull 14. A functional component 1406 is disposed within soft tissue implant 1404. Shown as part of the functional component 1406 are a diaphragm 1412, two MRI-lucent electro-osmotic pumps 1418, and a plurality of catheters 1414 which extend from functional component 1406 into brain tissue 16 so as to enable the delivery of desired substances into the brain tissue. While not shown in FIG. 14, functional component 1406 may include all components described above with respect to functional component 1300.

Additionally, a rechargeable battery of functional component 1406 may be charged by a wireless charging device 1430, which may be located within or under a pillow 18 of a patient. A Bluetooth or other wireless communication component of functional component 1406 may further be in communication with software 1440 executed on a mobile computing device or personal computing device 20. The software 1440 may be adapted to show real-time data from functional component 1406. Real-time data, such as flow rate information, residual battery life, medicine reservoir fill amounts, and potential flow malfunction, could all be transferred in real-time. In addition, the current design algorithm for this medicine delivery device includes an alternating rhythm of 16-20 hours pump-on, followed by alternating brain relaxation times of 4-8 hours off.

Furthermore, in some exemplary embodiments, both the bone implant and the soft tissue implant may include cavities therein for embedded functional devices, similar to the embodiments described above.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A functional, anatomy-specific craniofacial implant, comprising:
    a soft tissue implant adapted to replace missing soft tissue and occupy a soft tissue space proximate a pterional region of a cranium, the soft tissue implant being coupled to a rigid component; and
    a high-profile functional component embedded within an interior space of a body of the soft tissue implant, the functional component having at least one catheter for delivery of medicine to a brain;
    wherein the rigid component is one of a hard tissue implant and a cranial bone;
    the soft tissue implant is not patient-specific; and
    the soft tissue implant is anatomy-specific.

2. The implant of claim 1, further comprising:
    a hard tissue implant adapted to replace missing bone and occupy a hard tissue space of the pterional region of the cranium;
    wherein the hard tissue implant is not patient-specific; and
    the hard tissue implant is anatomy-specific.

3. The implant of claim 1, wherein the soft tissue space is one or more of a temporalis muscle, a temporal fat pad, and temporal subcutaneous tissue.

4. The implant of claim 1, wherein the functional component comprises a housing, a refillable reservoir, and at least one electro-osmotic pump.

5. The implant of claim 4, wherein a diaphragm of the reservoir protrudes above a surface of the housing.

6. The implant of claim 4, wherein the functional implant further comprises a processor, a wirelessly rechargeable battery, and a wireless communications device.

7. The implant of claim 1, wherein the soft tissue implant is coupled to one of the hard tissue implant and the cranial bone by an interdigitated connection.

8. The implant of claim 1, wherein the soft tissue implant is interchangeable with another soft tissue implant in a plug-and-play fashion.

9. A functional, anatomy-specific craniofacial implant, comprising:
    a hard tissue implant adapted to replace missing bone and occupy a hard tissue space of the pterional region of a cranium;
    a soft tissue implant adapted to replace missing soft tissue and occupy a soft tissue space proximate a pterional region of a cranium, the soft tissue implant being coupled to the hard tissue implant; and
    a high-profile functional component embedded within an interior space of a body of the soft tissue implant, the functional component having at least one catheter for delivery of medicine to a brain;
    wherein the hard tissue implant and the soft tissue implant are not patient-specific; and
    the hard tissue implant and the soft tissue implant are anatomy-specific.

10. The implant of claim 9, wherein the soft tissue space is one or more of a temporalis muscle, a temporal fat pad, and temporal subcutaneous tissue.

11. The implant of claim 9, wherein the functional implant comprises a housing, a refillable reservoir, and at least one electro-osmotic pump.

12. The implant of claim 11, wherein a diaphragm of the reservoir protrudes above the surface of the housing.

13. The implant of claim 11, wherein the functional implant further comprises a processor, a wirelessly rechargeable battery, and a wireless communications device.

14. The implant of claim 9, wherein the soft tissue implant is coupled to the hard tissue implant by an interdigitated connection.

15. The implant of claim 9, wherein the soft tissue implant is interchangeable with another soft tissue implant in a plug-and-play fashion.

* * * * *